United States Patent
Yamada et al.

(10) Patent No.: US 6,294,568 B1
(45) Date of Patent: Sep. 25, 2001

(54) 5-ARYLPYRROLE DERIVATIVES

(75) Inventors: Toshihiro Yamada, Moriyama; Yoichi Nobuhara, Aioi; Kazuhiro Kobayashi; Satoshi Hirano, both of Otsu; Takanobu Sakurai, Kurita-gun; Hiroshi Mikami, Otsu; Ayako Miyake, Chofu, all of (JP)

(73) Assignee: Nissin Food Products Co., Ltd., Osaka (JP)

( * ) Notice: Subject to any disclaimer, the term of this patent is extended or adjusted under 35 U.S.C. 154(b) by 0 days.

(21) Appl. No.: 09/582,411

(22) PCT Filed: Dec. 25, 1998

(86) PCT No.: PCT/JP98/05972

§ 371 Date: Jun. 26, 2000

§ 102(e) Date: Jun. 26, 2000

(87) PCT Pub. No.: WO99/33796

PCT Pub. Date: Jul. 8, 1999

(30) Foreign Application Priority Data

Dec. 26, 1997 (JP) .................................................. 9-359171

(51) Int. Cl.$^7$ .......................... A61K 31/40; A61P 29/02; C07D 207/323; C07D 207/333

(52) U.S. Cl. .......................... 514/415; 514/427; 514/444; 514/464; 514/557; 548/469; 548/531; 548/543; 548/550; 548/551; 548/560; 548/561; 548/562; 549/59; 549/430; 549/434; 549/435; 562/405; 562/492; 424/452; 424/465; 424/489

(58) Field of Search .................................... 514/415, 427; 548/469, 531, 543

(56) References Cited

U.S. PATENT DOCUMENTS

| | | | |
|---|---|---|---|
| 4,267,184 | 5/1981 | Cherkofsky | 424/263 |
| 4,267,190 | 5/1981 | Cherkofsky | 424/274 |
| 4,318,917 | 3/1982 | Cherkofsky et al. | 424/274 |
| 4,335,136 | 6/1982 | Cherkofsky | 424/274 |
| 4,477,463 | 10/1984 | Cherkofsky | 424/274 |
| 4,652,582 | 3/1987 | Wilkerson | 514/427 |

FOREIGN PATENT DOCUMENTS

| | | |
|---|---|---|
| 537 923 | 6/1973 | (CH) . |
| 0 025 884 | 4/1981 | (EP) . |
| 0 038 536 | 10/1981 | (EP) . |

OTHER PUBLICATIONS

Wilkerson, Wendell W. et al., "Antiinflammatory 4,5–Diarylpyrroles. 2. Activity as a Function of Cyclooxygenase–2 Inhibition", J. Med. Chem., 38(20), 3895–3901 (1995) (Copy submitted to USPTO by WIPO).

Wilkerson, Wendell W. et al., "Antiinflammatory 4,5–Diarylpyrroles: Synthesis and QSAR", J. Med. Chem., 37(7), 988–98 (1994) (Copy submitted to USPTO by WIPO).

International Search Report (Jan. 17, 2000).

Journal of Medicinal Chemistry, vol. 38, No. 20, pp. 3895–3901 (1995).

Journal of Medicinal Chemistry, vol. 37, No. 7, pp. 988–998 (1994).

Medicinal Chemistry Research, vol. 5, pp. 399–408 (1995).

Research Disclosure, Jun. 1986, pp. 323–324.

Japanese Examined Patent Publication No. 1973–38704, published Nov. 19, 1973.

Primary Examiner—Joseph K. McKane
Assistant Examiner—Jane C. Osowecki
(74) Attorney, Agent, or Firm—Sughrue, Mion, Zinn, Macpeak & Seas, PLLC

(57) ABSTRACT

The present invention provides compounds represented by the general formula (I):

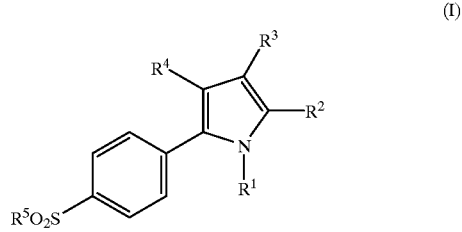

(I)

and a salt thereof, and anti-inflammatory agents and antitumor agents containing the compounds as the active ingredients.

16 Claims, No Drawings

5-ARYLPYRROLE DERIVATIVES

This application is a 371 of PCT/JP98/05972 filed Dec. 25, 1998.

TECHNICAL FIELD

The present invention relates to 5-arylpyrrole derivatives such as 4,5-diarylpyrrole derivatives having anti-inflammatory action, antipyretic action, analgesic action, antirheumatic action, and cytostatic action and to anti-inflammatory agents and antitumor agents which contain the derivatives as active ingredients.

BACKGROUND ART

Various compounds of 4,5-diarylpyrrole derivatives are known (see, for example, Japanese Unexamined Patent Publication No. 54-79271 (1979); U.S. Pat. No. 4,652,582; Japanese Patent Publication No. 48-38704 (1973)).

Nonsteroidal anti-inflammatory agents serve to inhibit cyclooxygenase (COX) in its mechanism of action. Cyclooxygenase is known to have two subtypes, i.e., cyclooxygenase-1 (COX-1) and cyclooxygenase-2 (COX-2), and conventional nonsteroidal anti-inflammatory agents inhibit both the subtypes. COX-1 is constantly present in gastrointestinal tract and so on and causes adverse side effects such as gastrointestinal disorders when inhibited. On the other hand, COX-2 appears only when an inflammation occurs and, therefore, a compound which selectively inhibits COX-2 is expected as a drug with minimal side effects [Mebio, Vol. 11, No. 10, p. 80 (1994)]. Further, it has been reported that COX-2 is involved in proliferation of colon cancer and, therefore, the COX-2 selective inhibitor is also expected as an antitumor agent (CANCER RESEARCH, Vol. 55, 3785 (1995)).

The compounds of the above-mentioned conventional techniques exhibit strong anti-inflammatory action; however, there has been a problem of adverse side effects such as gastrointestinal tract disorders since the compounds do not have selectivity with respect to the cyclooxygenase or, even if the selectivity is known, the inhibitory activity is insufficient.

Among 4,5-diarylpyrrole derivatives, examples of the compounds whose COX-2 inhibitory activity is described are found in J. Med. Chem., Vol. 38, 3895 (1995), Med. Chem. Res., Vol. 5, No. 5, 399 (1995), J. Med. Chem., Vol. 37, 988 (1994). In the literatures, the enhanced anti-inflammatory action is realized mainly by introducing electron withdrawing groups on 2- and 3-positions of 4,5-diarylpyrrole; however, the selective inhibitory activity of COX-2 is rather suppressed in the compounds to which the electron withdrawing groups are introduced as substituents than, for example, that of the compounds wherein the 2- and 3-positions of 4,5-diarylpyrrole are hydrogen atoms. Further, the literatures do not disclose any examples of electron donating groups as the substituents for the 2- and 3-positions. Moreover, no description of the cytostatic action is given in the literatures.

The object of the present invention is to provide an anti-inflammatory agent and antitumor agent which selectively inhibit COX-2 without adverse side effects such as gastric disorder.

The present invention relates to compounds represented by General Formula (1):

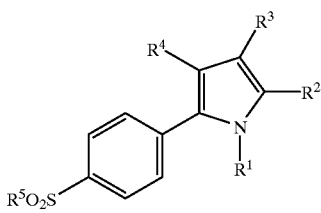

wherein,
$R^1$ represents a hydrogen atom or lower alkyl group.
$R^2$ represents a lower alkyl group or $(CH_2)_{n1}COOH$ and n1 is 1, 2 or 3.
$R^3$ represents a hydrogen atom, halogen atom, lower alkyl group, hydroxymethyl group, carboxyl group (COOH), lower alkoxycarbonyl group, lower alkoxymethyl group, carbamoyl group ($CONH_2$), mono-lower alkylcarbamoyl group or di-lower alkylcarbamoyl group.
$R^4$ represents a phenyl group, bicyclic heteroaryl group or phenyl ethynyl group which may optionally be substituted by a functional group selected from the group consisting of a lower alkyl group, halogen atom, lower alkoxy group, lower alkylthio group, nitro group, alkanoyl group, cyano group, amino group, mono-lower alkylamino group, di-lower alkylamino group, alkanoylamino group and alkanoyloxy group; or lower alkynyl group.
$R^5$ represents a lower alkyl group, amino group, mono-lower alkylamino group or di-lower alkylamino group, and a salt thereof; and an anti-inflammatory agent and antitumor agent which comprise said compounds as the active ingredients.

Examples of the lower alkyl group include $C_1$–$C_6$ alkyl groups having linear or branched chain, such as methyl, ethyl, n-propyl, isopropyl, n-butyl, isobutyl, sec-butyl, t-butyl, pentyl and hexyl group.

Examples of the halogen atom include a chlorine atom, bromine atom, fluorine atom and iodine atom. Examples of the lower alkoxycarbonyl group include $C_1$–$C_6$ alkoxycarbonyl groups having linear or branched chain, such as a methoxycarbonyl, ethoxycarbonyl, n-propoxycarbonyl, i-propoxycarbonyl, n-butoxycarbonyl, i-butoxycarbonyl, sec-butoxycarbonyl and t-butoxycarbonyl. Examples of the lower alkoxy group include $C_1$–$C_6$ alkoxy groups having linear or branched chain such as methoxy, ethoxy, n-propoxy, i-propoxy, n-butoxy, i-butoxy, sec-butoxy and t-butoxy.

Examples of the lower alkoxymethyl group include $C_2$–$C_5$ lower alkoxymethyl groups, such as methoxymethyl, ethoxymethyl, isopropoxymethyl and t-butoxymethyl.

Examples of the mono-lower alkylcarbamoyl group include $C_2$–$C_5$ alkylcarbamoyl groups, such as methylcarbamoyl, ethylcarbamoyl, n-propylcarbamoyl, i-propylcarbamoyl and n-butylcarbamoyl.

Examples of the di-lower alkyl carbamoyl group include $C_3$–$C_9$ dialkylcarbamoyl groups, such as dimethylcarbamoyl, diethylcarbamoyl, di(n-propyl) carbamoyl and di(n-butyl)carbamoyl.

Examples of the lower alkylthio group include $C_1$–$C_6$ alkylthio groups having linear or branched chain, such as methylthio, ethylthio, n-propylthio, isopropylthio, n-butylthlo, isobutylthio, sec-butylthio, t-butylthio, pentylthio and hexylthio.

Examples of the lower alkanoyl group include $C_1$–$C_4$ alkanoyl groups, such as formyl, acetyl, propionyl and butyryl.

Examples of the mono-lower alkylamino group include $C_1$–$C_6$ monoalkylamino groups having linear or branched chain, such as methylamino, ethylamino, n-propylamino, isopropylamino, n-butylamino, isobutylamino, sec-butylamino, t-butylamino, pentylamino and hexylamino.

Examples of the di-lower alkylamino group include amino groups which are di-substituted by $C_1$–$C_4$ alkyl groups having linear or branched chain, such as dimethylamino, diethylamino, di-n-propylamino, disopropylamino, di-n-butylamino, diisobutylamino, di-sec-butylamino and di-t-butylamino.

Examples of the alkanoylamino group include $C_1$–$C_4$ alkanoylamino groups, such as formylamino, acetylamino, propionylamino and butyrylamino.

Examples of the alkanoyloxy groups include $C_2$–$C_4$ alkanoyloxy groups, such as acetyloxy, propionyloxy and butyryloxy.

Where the phenyl group represented by $R^4$ is mono-substituted by any one of said functional groups, the substitution position may be 2-, 3- or 4-position, preferably 3- or 4-position, and more preferably 4-position. In the case of di-substitution, the substitution positions may be 2- and 3-positions, 2- and 4-positions, 2- and 5-positions, 3- and 5-positions or 3- and 4-positions, preferably 2- and 4-positions or 3- and 4-positions. In the case of tri-substitution, the substitution positions may preferably be 2-, 3- and 4-positions or 3-, 4- and 5-positions. Examples of preferable substituents include a lower alkyl, lower alkoxy, halogen atom, amino, mono- or di-lower alkylamino and lower alkylthio group.

Examples of the bicyclic heteroaryl group which may optionally be substituted by any one of said functional groups preferably include 6-indolyl, 6-N-methylindolyl, 5-indolyl, 5-N-methylindolyl, 5-(2,3-dihydrobenzofuranyl), 6-(2,3-dihydrobenzofuranyl), 4-(3,4-methylenedioxyphenyl) and 3-(3,4-methylenedioxyphenyl). The bicylic heteroaryl group is a group whose one ring is a benzene ring and the other ring is a 5-membered or 6-membered ring containing 1 or 2 hetero atoms, N, O or S. Examples of substituents for the bicyclic heteroaryl group include the functional groups, i.e., a lower alkyl group, halogen atom, lower alkoxy group, lower alkylthio group, nitro group, alkanoyl group, cyano group, amino group, mono-lower alkylamino group, di-lower alkylamino group, alkanoylamino group, and alkanoyloxy group, preferably a lower alkyl, halogen atom, hydroxyl group, lower alkoxy, amino, mono- or di-lower alkylamino, lower alkylthio and, in particular, a methyl group.

Examples of substituents for the phenylethynyl group include said functional groups, i.e., a lower alkyl group, halogen atom, lower alkoxy group, lower alkylthio group, nitro group, alkanoyl group, cyano group, amino group, mono-lower alkylamino group, di-lower alkylamino group, alkanoylamino group, and alkanoyloxy group, preferably a lower alkyl, halogen atom, lower alkoxy, amino, mono- or di-lower alkylamino, lower alkylthio and, in particular, a methyl group.

Examples of the alkynyl groups include $C_2$–$C_6$ alkynyl groups, such as ethynyl group, propynyl group, butynyl group, pentynyl group and hexynyl group.

Examples of substituents for the phenylethynyl group include said functional groups, preferably a lower alkyl, lower alkoxy, halogen atom, amino, mono- or di-lower alkylamino, and lower alkylthio.

$R^1$ preferably represents a hydrogen atom, methyl or ethyl, more preferably a hydrogen atom or methyl, particularly preferably a hydrogen atom.

Preferable $R^2$ may be a lower alkyl group, in particular, a methyl group.

Preferable $R^3$ may be a hydrogen atom.

Preferable $R^4$ may be a phenyl which is mono-substituted or di-substituted by any one of said functional groups, 6-indolyl, 6-N-methylindolyl, 5-indolyl, 5-N-methylindolyl, 5-(2,3-dihydrobenzofuranyl), 6-(2,3-dihydrobenzofuranyl), 4-(3,4-methylenedioxyphenyl), 3-(3,4-methylenedioxyphenyl), phenylethynyl, ethynyl and propynyl.

Particularly preferably, $R^4$ may be a lower alkyl, lower alkoxy, halogen atom, amino group, mono- or di-lower alkylamino, phenyl group which is mono-substituted or di-substituted by a lower alkylthio, 6-N-methylindolyl, 5-N-methylindolyl, 5-(2,3-dihydrobenzofuranyl), 6-(2,3-dihydrobenzofuranyl) or phenylethynyl group.

Preferable $R^5$ may be methyl, $NH_2$ or NHMe, more preferably methyl or $NH_2$, and particularly preferably methyl.

Compounds of the General Formula (1) of the present invention can be prepared, for example, in accordance with the following <Reaction Scheme 1>.

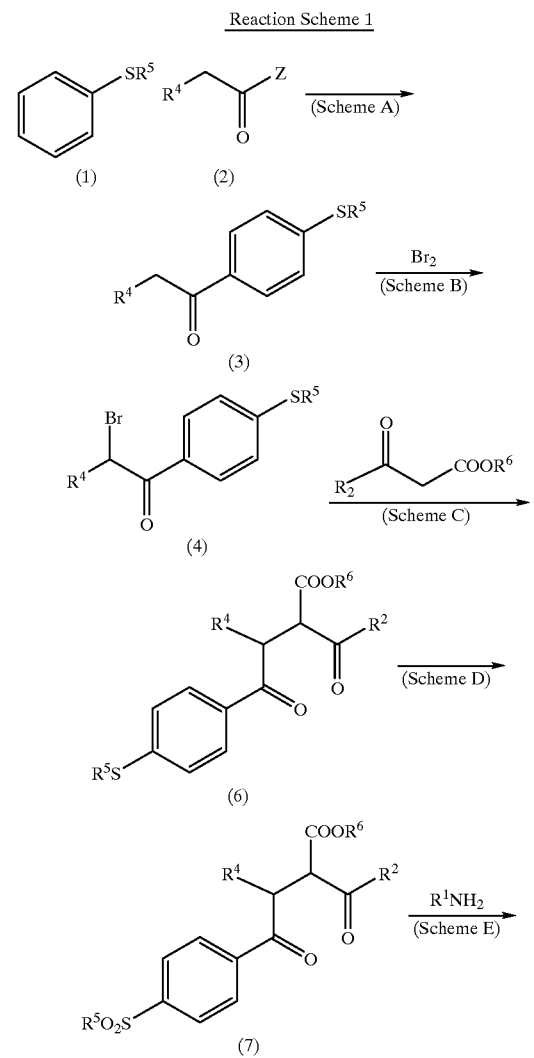

Reaction Scheme 1

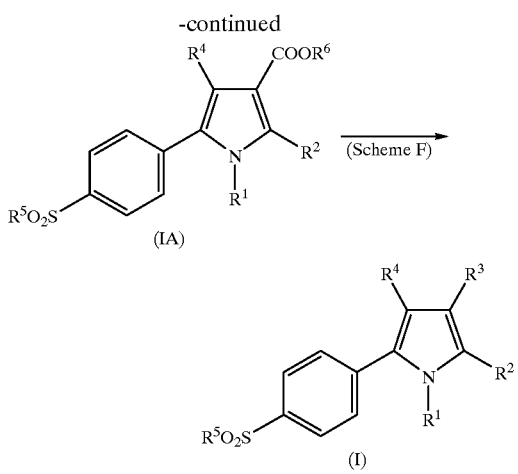

wherein,

- $R^1$ represents a hydrogen atom or lower alkyl group.
- $R^2$ represents a lower alkyl group or $(CH_2)_{n1}$ COOH and n1 is 1, 2 or 3.
- $R^3$ represents a hydrogen atom, halogen atom, lower alkyl group, hydroxymethyl group, carboxyl group (COOH), lower alkoxycarbonyl group, lower alkoxymethyl group, carbamoyl group ($CONH_2$), mono-lower alkylcarbamoyl group or di-lower alkylcarbamoyl group.
- $R^4$ represents a phenyl group, bicyclic heteroaryl group or phenylethynyl group which may optionally be substituted by a functional group or groups selected from the group consisting of a lower alkyl group, halogen atom, lower alkoxy group, lower alkylthio group, nitro group, alkanoyl group, cyano group, amino group, mono-lower alkylamino group, di-lower alkylamino group, alkanoylamino group and alkanoyloxy group; or lower alkynyl group,
- $R^5$ represents a lower alkyl group,
- $R^6$ represents a hydrogen atom or lower alkyl group, and
- Z represents a halogen atom.

(Scheme A)

The compound (3) can be prepared by the reaction of the compound (1) with 1–2 equivalents of the acid halide (2) in the presence of an acid catalyst at temperatures from a room temperature to about 100° C. at a flux temperature of a solvent for 1–24 hours. Examples of the acid catalyst to be used in the reaction include an alminium chloride and the like.

The reaction is generally conducted in a solvent, and examples of the solvent include a dichloromethane, chloroform, carbon disulfide, nitrobenzene, chlorobenzene and the like.

(Scheme B)

The brominated compound (4) can be prepared by he reaction of the compound (3) with 1 equivalent of bromine at temperatures from an ice cold temperature to a room temperature for 1–24 hours.

The reaction can be conducted in the absence of a solvent or in one of the solvents properly selected from dioxane, tetrahydrofran, diethylether, n-hexane, cyclohexane, dichloromethane, chloroform and the like.

(Scheme C)

The compound (6) can be prepared by the reaction of the brominated compound (4) with 1–2 equivalents of the compound (5) or a salt thereof in the presence of a base at temperatures from a room temperature to 100° C. or a reflux temperature of a solvent for 1–24 hours.

Examples of the base to be used in the present reaction include alkali metal hydroxides such as lithium hydroxide, potassium hydroxide and sodium hydroxide, alkali metal carbonates such as sodium carbonate and potassium carbonate, alkali metal hydrogencarbonates such as sodium hydrogencarbonate and potassium hydrogencarbonate, alkali metal hydrides such as sodium hydride and potassium hydride, inorganic bases such as sodium and sodium amide, organic bases such as triethylamine tri-n-butylamine, pyridine and N,N-dimethylaminopyridine or the like.

Further, examples of the salt to be used in the reaction include a sodium salt and potassium salt. The reaction can be conducted in the absence of a solvent or in a solvent properly selected from dioxane, a tetrahydrofuran, diethylether, n-hexane, cyclohexane, dichloromethane chloroform, ethyl acetate, benzene, xylene, acetone, acetonitrile, N,N-dimethylformamide, dimethysufoxide, water and the like.

(Scheme D)

The sulfonic compound (7) can be prepared by the reaction of the compound (6) with 1 equivalent to an excessive amount of an oxidizing agent at temperatures from an ice cold temperature to about 100° C. for 1–24 hours.

The oxidation can be carried out, for example, by a method using an oxidizing agent such as a hydrogen peroxide or 3-chloroperbenzoic acid to allow an alkylthio group to be oxidized into an alkylsulfonyl group.

The solvent to be used in the reaction may be properly selected depending on the oxidizing method employed. Generally, solvents such as dioxane, tetrahydrofuran, diethylether, n-hexane, cyclohexane, dichloromethane, chloroform, benzene, xylene and the like are employed in the reaction.

(Scheme E)

The compound of the formula (IA) can be prepared by the reaction of the sulfon compound (7) with 1 equivalent to an excessive amount of the amino compound represented by $R^1NH_2$ or an ammonium salt at temperatures from a room temperature to about 100° C. or at a reflux temperature of a solvent for 1–24 hours.

Examples of the amino compound and ammonium salt to be used in the reaction include a methylamine hydrochloride, ethylamine, n-propylamine, isopropylamine, n-butylamine, s-butylamine, t-butylamine, ammonium carbonate and ammonium acetate and the like.

The reaction can be conducted in the absence of a solvent or in a solvent properly selected from dioxane, tetrahydrofuran, diethylether, n-hexane, cyclohexane, dichloromethane chloroform, benzene, xylene and the like.

(Scheme F)

A carboxylic compound wherein $R^3$ is a carboxyl group can be obtained by hydrosis of the compound of the Formula (IA) in the presence of an acid or base. The compound (I) of the invention wherein $R^3$ is a hydrogen atom can be prepared by decarboxylation wherein the carboxylic compound is reacted in the presence of an acid at temperatures from a room temperature to 150° C. for 1–24 hours or by decarboxylation wherein the carboxylic compound is heated in the presence of a base at temperatures from a room temperature to 200° C.

Further, the compound (I) of the invention wherein $R^3$ is a halogen atom can be prepared by the reaction of the compound of the Formula (I) with a halogenating reagent (halogen or N-succinimide halide) at temperatures from a room temperature to 100° C. or approximately at a reflux temperature of a solvent for 1–24 hours. The reaction can be conducted in the absence of a solvent or in a solvent properly selected from dioxane, tetrahydrofuran, ethylether, n-hexane, cyclohexane, dichloromethane, chloroform and the like.

The compound of the invention wherein $R^3$ is a hydroxymethyl group can be prepared by the reaction of the compound of the Formula (IA) with 1–2 equivalents of a reducing agent at temperatures from a room temperature to 100° C. or approximately at a reflux temperature of a solvent for 1–24 hours. The compound of the invention may be further reacted with a halogenating agent such as thionyl chloride at temperatures from a room temperature to 100° C. or approximately at a reflux temperature of a solvent for 1–24 hours, then reacted with 1–2 equivalents of a reducing agent at temperatures from a room temperature to 100° C. or approximately at a reflux temperature of the solvent for 1–24 hours to obtain the compound of the invention wherein $R^3$ is a methyl group.

Furthermore, the compound of the invention wherein $R^3$ represents a carbamoyl group or methyl-, ethyl-, n-propyl-, i-propyl-, n-butyl-, dimethyl-, diethyl-, di-n-propyl-, di-i-propyl-, di-n-butyl- and like mono- or di-lower alkyl-carbamoyl group can be prepared by the reaction of the compound of the Formula (IA) with ammonia or methyl-, ethyl-, n-propyl-, i-propyl-, n-butyl-, dimethyl-, diethyl-, di-n-propyl-, di-i-propyl-, di-n-butyl- and like mono- or di-lower alkylamine or a salt thereof in the presence of 1–2 equivalents of a condensating agent at temperatures from a room temperature to 100° C. or approximately at a reflux temperature of the solvent for 1–24 hours.

Examples of the acid to be used in the reaction are inorganic acids such as sulfuric acid, hydrochloric acid and nitric acid or organic acids such as acetic acid, citric acid, oxalic acid, lactic acid and butyric acid. Examples of the base to be used in the present reaction include alkali metal hydroxides such as lithium hydroxide, potassium hydroxide and sodium hydroxide, alkali metal carbonates such as sodium carbonate and potassium carbonate, alkali metal hydrogencarbonates such as a sodium hydrogencarbonate and potassium hydrogencarbonate, alkali metal hydrides such as sodium hydride and potassium hydride, inorganic bases such as sodium and sodium amide, organic bases such as triethylamine, tri-n-butylamine, pyridine and N,N-dimethylaminopyridine or the like.

The reduction can be carried out by a method which allows an ester to be reduced into an alcohol and a method of dehalogenating an alkyl halide, wherein a lithium alminium hydride, sodium borohydride, sodium cyano borohydride and the like are employed.

Examples of the condensating agent to be used in the reaction are dicyclohexylcarbodiimide, water soluble carbodiimide, potassium carbonate, sodium hydroxide, potassium hydroxide, p-toluenesulfonic acid, sulfuric acid and the like.

The reaction can be conducted in the absence of a solvent or in a solvent properly selected from dioxane, tetrahydrofuran, diethylether, n-hexane, cyclohexane, dichloromethane chloroform, benzene, xylene, acetonitrile, N,N-dimethylformamide, dimethylsulfoxide and the like. Further, the compound (3) can alternatively be prepared by the preparation scheme of (Scheme G) shown in the following <Reaction Scheme 2>.

Reaction Scheme 2

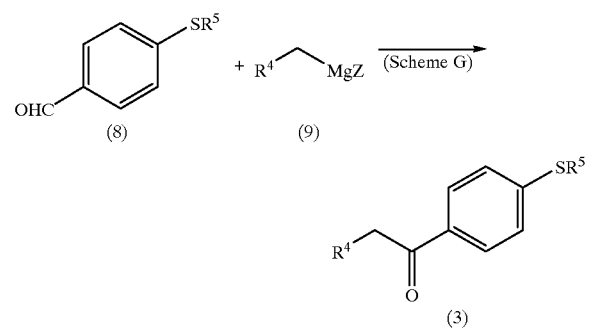

wherein, $R^4$ and $R^5$ are as defined above. Z represents a halogen atom.

(Scheme G)

The compound (3) can be prepared by the reaction of compound (8) with 1–2 equivalents of magnesium halide (9) at temperatures from a room temperature to about 100° C. or approximately at a reflux temperature of the solvent for 1–24 hours.

The reaction can be conducted in the absence of a solvent or in a solvent properly selected from dioxane, tetrahydrofuran, diethylether, n-hexane, cyclohexane and the like.

Further, the compound (I) of the invention can be prepared also by the preparation schemes of (Scheme H) to (Scheme J) shown in the following <Reaction Scheme 3>.

Reaction Scheme 3

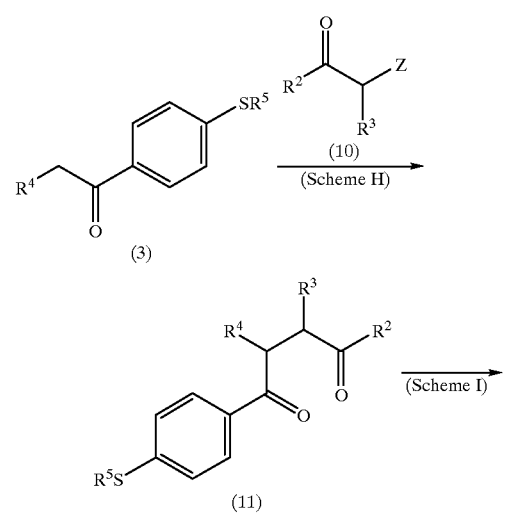

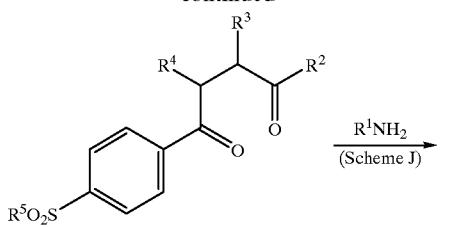

(12)

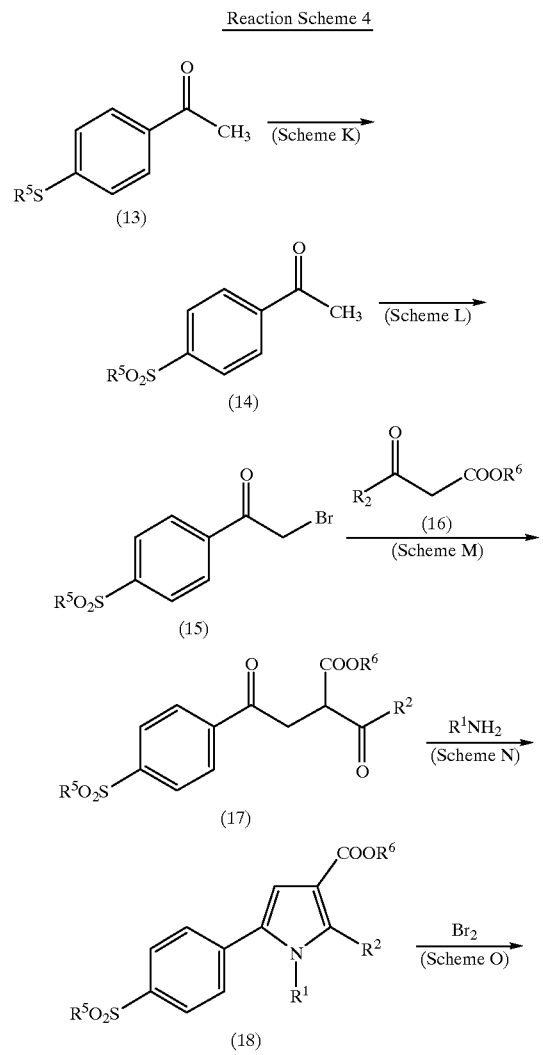

wherein,

R$^1$ to R$^5$ are as defined above. Z represents a halogen atom.

(Scheme H)

1,4-diketone compound (11) can be prepared by the reaction of the compound (3) obtained in the above schemes with 1–2 equivalents of a -haloketone (10) in the presence of 1 equivalent to an excessive amount of a base at temperatures from a room temperature to 100° C. or at a reflux temperature of the solvent for 1–24 hours.

Examples of the base to be used in the present reaction include alkali metal hydroxides such as lithium hydroxide, potassium hydroxide and sodium hydroxide, alkali metal carbonates such as sodium carbonate and potassium carbonate, alkali metal hydrogencarbonates such as a sodium hydrogencarbonate and potassium hydrogencarbonate, alkali metal hydrides such as sodium hydride and potassium hydride, inorganic bases such as sodium potassium and sodium amide, organic bases such as triethylamine, tri-n-butylamine, pyridine and N,N-dimethylaminopyridine or the like.

The reaction can be conducted in the absence of a solvent or in a solvent properly selected from dioxane, tetrahydrofuran, diethylether, n-hexane, cyclohexane, dichloromethane chloroform, ethyl acetate, benzene, xylene, acetone, acetonitrile, N,N-dimethylformamide, dimethylsulfoxide and the like.

(Scheme I)

The sulfonic compound (12) can then be prepared by the reaction of the 1,4-diketone compound (11) with 1 equivalent to an excessive amount of an oxidizing agent at temperatures from an ice cold temperature to approximately the reflux temperature of the solvent for 1–24 hours.

The oxidation can be carried out, for example, by a method using an oxidizing agent such as hydrogen peroxide or 3-chloroperbenzoic acid to allow an alkylthio group to be oxidized into an alkylsulfonyl group. The solvent used in the reaction may be properly selected depending on the oxidizing method employed. Generally, solvents such as dioxane, tetrahydrofuran, diethylether, n-hexane, cyclohexane, dichloromethane, chloroform, benzene, xylene and the like are employed in the reaction.

(Scheme J)

Finally, the compound (I) of the invention can be prepared by the reaction of the sulfonic compound (12) with 1–2 equivalents of the amino compound represented by R$^1$NH$_2$ or an ammonium salt at temperatures from a room temperature to 100° C. or approximately at a reflux temperature of the solvent for 1–24 hours.

Examples of the amine to be used in the reaction are methylamine, ethylamine, n-propylamine isopropylamine, n-butylamine, s-butylamine, t-butylamine and the like. Examples of the ammonium salt to be used in the reaction are ammonium carbonate, ammonium acetate and the like.

The reaction can be conducted in the absence of a solvent or in a solvent properly selected from dioxane, tetrahydrofuran, diethylether, n-hexane, cyclohexane, dichloromethane, chloroform, ethyl acetate, benzene, xylene, acetone, acetonitrile, N,N-dimethylformamide, dimethylsulfoxide, water and the like.

Further, the compound (I) of the invention can alternatively be synthesized by the preparation schemes of (Scheme K) to (Scheme Q) shown in the following <Reaction Scheme 4>.

Reaction Scheme 4

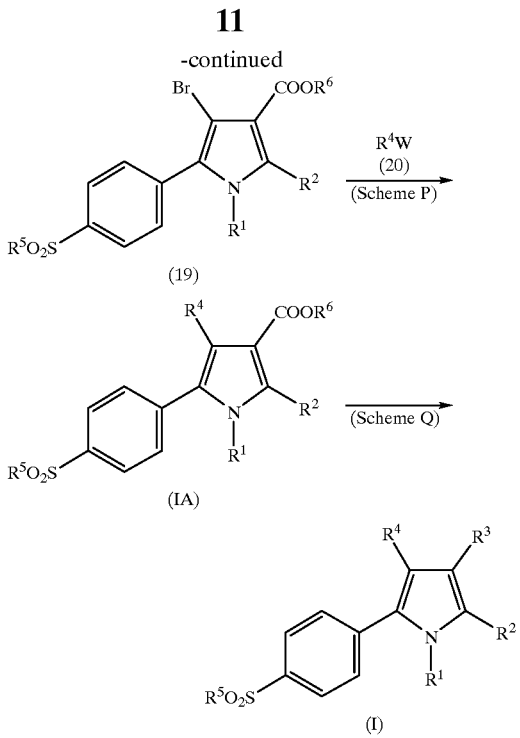

wherein,

R¹, R², R³, R⁴, R⁵, and R⁶ are as described above. W represents $B(OH)_2$ or $Sn(n-Bn)_3$.

(Scheme K)

The compound (14) can be prepared by the reaction of the compound (13) with 1 equivalent to an excessive amount of an oxidizing agent at temperatures from an ice cold temperature to about 100° C. for 1–24 hours.

The oxidation can be carried out, for example, by a method using an oxidizing agent such as hydrogen peroxide or 3-chloroperbenzoic acid to allow an alkylthio group to be oxidized Into an alkylsulfonyl group. The solvent to be used in the reaction may be properly selected depending on the oxidizing method employed. Generally, the solvent such as dioxane, tetrahydrofuran, diethylether, n-hexane, cyclohexane, dichloromethane, chloroform, benzene, xylene and the like are employed in the reaction.

(Scheme L)

The α-bromoketone compound (15) can be prepared by the reaction of the compound (14) with about equivalent of bromine at temperatures from an ice cold temperature to about 100° C. for 1–24 hours.

The reaction can be conducted in the absence of a solvent or in a solvent properly selected from dioxane, tetrahydrofuran, diethylether, n-hexane, cyclohexane, dichloromethane, chloroform, benzene, xylene and the like.

(Scheme M)

The compound (17) can be prepared by the reaction of the α-bromoketone compound (15) with 1–2 equivalents of the compound (16) or a salt thereof in the presence of 1 equivalent to an excessive amount of a base at temperatures from an ice cold temperature to about 100° C. for 1–24 hours.

Examples of the base to be used in the reaction include alkali metal hydroxides such as lithium hydroxide, potassium hydroxide and sodium hydroxide, alkali metal carbonates such as sodium carbonate and potassium carbonate, alkali metal hydrogencarbonates such as sodium hydrogencarbonate and potassium hydrogencarbonate, alkali metal hydrides such as sodium hydride and potassium hydride, inorganic bases such as sodium and sodium amide, organic bases such as triethylamine, trl-n-butylamine, pyridine and N,N-dimethylaminopyridine or the like.

Further, examples of the salt to be used in the reaction are sodium salt, potassium salt and the like.

The reaction can be conducted in the absence of a solvent or in a solvent properly selected from dioxane, tetrahydrofuran, diethylether, n-hexane, cyclohexane, dichloromethane, chloroform, benzene, xylene, N,N-dimethylformamide, dimethylsulfoxide and the like.

(Scheme N)

The compound (18) can be prepared by the reaction of the compound (17) with 1–2 equivalents of the amino compound represented by $R^1NH_2$ or an ammonium salt at temperatures from a room temperature to 100° C. or approximately at a reflux temperature of a solvent for 1–24 hours.

Examples of the amine to be used in the reaction are methylamine, ethylamine, n-propylamine, isopropylamine, n-butylamine, s-butylamine, t-butylamine and the like. Examples of the ammonium salt employed in the reaction are ammonium carbonate, ammonium acetate and the like.

The reaction can be conducted in the absence of the solvent or in a solvent properly selected from dioxane, tetrahydrofuran, diethylether, n-hexane, cyclohexane, dichloromethane, chloroform, benzene, xylene, N,N-dimethylformamide, dimethylsulfoxide, water and the like.

(Scheme O)

The compound (19) can be prepared by the reaction of the compound (18) with 1 equivalent of bromine at temperatures from an ice cold temperature to about 100° C. for 1–24 hours.

The reaction can be conducted in the absence of a solvent or in a solvent properly selected from dioxane, tetrahydrofuran, diethylether, n-hexane, cyclohexane, dichloromethane, chloroform, benzene, xylene, N,N-dimethylformamide, dimethylsulfoxide, methanol, ethanol, n-propanol, isopropanol and the like.

(Scheme P)

The compound represented by the Formula (IA) can be prepared by the reaction of the compound (19) with 1–2 equivalents of the compound (20) and 1 equivalent of an aqueous base solution such as a sodium carbonate solution in the presence of a catalyst at temperatures from a room temperature to 100° C. or approximately at a reflux temperature of the solvent for 1–24 hours.

The reaction can be conducted in a solvent properly selected from dioxane, tetrahydrofuran, diethylether, n-hexane, cyclohexane, dichloromethane, chloroform, benzene, xylene, N,N-dimethylformamide, dimethylsulfoxide, methanol, ethanol, n-propanol, isopropanol and the like. Examples of the catalyst to be used in the reaction are a tetrakistriphenylphosphinepalladium, bistriphenylphosphinepalladium chloride, zinc chloride and the like.

(Scheme Q)

Finally, the compound (I) of the invention can be prepared by treating the compound (IA) in the same manner as described in the Scheme F.

Examples of the acid to be used in the reaction are inorganic acids such as sulfuric acid, hydrochloric acid and nitric acid or organic acids such as acetic acid, citric acid, oxalic acid, lactic acid and butyric acid.

Examples of the base to be used in the reaction include alkali metal hydroxides such as lithium hydroxide, potassium hydroxide and sodium hydroxide, alkali metal carbonates such as sodium carbonate and potassium carbonate, alkali metal hydrogencarbonates such as sodium hydrogencarbonate and potassium hydrogencarbonate, alkali metal hydrides such as sodium hydride and potassium hydride, inorganic bases such as sodium and sodium amide, organic bases such as triethylamine, tri-n-butylamine, pyridine and N,N-dimethylaminopyridine or the like.

Further, the title compound (I) can alternatively be synthesized according to (Scheme R) to (Scheme Y) shown in the following <Reaction Scheme 5>.

Reaction Scheme 5

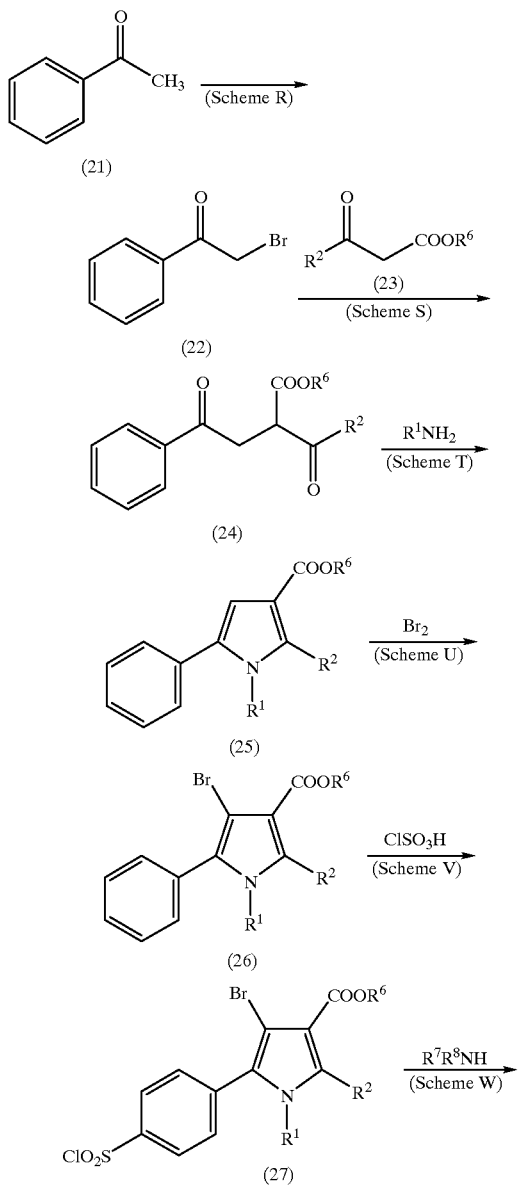

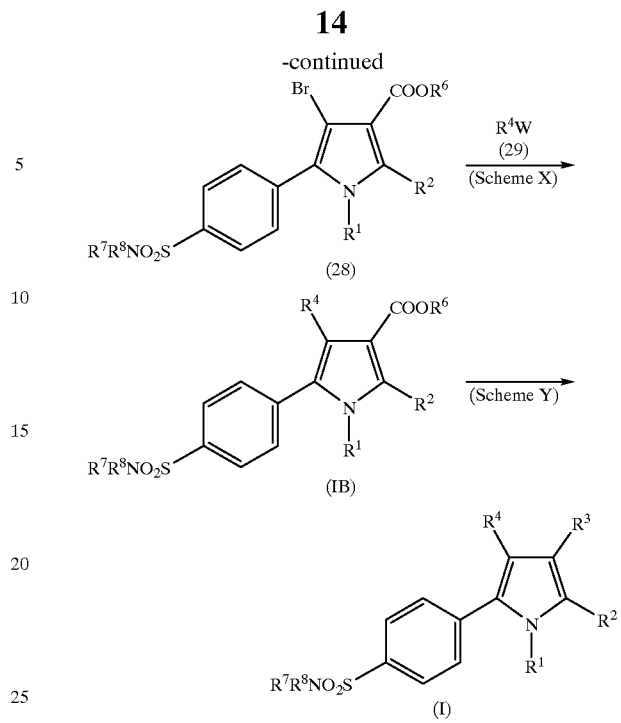

wherein, $R^1$, $R^2$, $R^3$, $R^4$ and $R^6$ are as defined above. $R^7$ and $R^8$ are the same or different and represent a hydrogen atom or lower alkyl group, and W represents $B(OH)_2$ or $Sn(n\text{-}Bu)_3$.

(Scheme R)

The compound represented by the formula (22) can be obtained by the reaction of 1 mol of the compound (21) with about 1 mol of bromine at temperatures from ice cold to about 100° C. for 1–24 hours.

The reaction can be conducted in the absence of a solvent or in a solvent properly selected from dioxane, tetrahydrofuran, ethylether, n-hexane, cyclohexane, dichloromethane, chloroform, benzene, xylene and the like.

(Scheme S)

The compound represented by the formula (24) can be prepared by the reaction of 1 mol of the compound of the formula (22) with 1 to 2 mol of the compound represented by the formula (23) or a salt thereof in the presence of 1 mol to an excessive amount of a base at temperatures from a room temperature to about 100° C. for 1–24 hours.

Examples of the base to be used in the reaction include alkali metal hydroxides such as lithium hydroxide, potassium hydroxide and sodium hydroxide, alkali metal carbonates such as sodium carbonate and potassium carbonate, alkali metal hydrogencarbonates such as sodium hydrogencarbonate and potassium hydrogencarbonate, alkali metal hydrides such as sodium hydride and potassium hydride, inorganic bases such as sodium and sodium amide, organic bases such as triethylamine, tri-n-butylamine, pyridine and N,N-dimethylaminopyridine or the like. Further, examples of the salt to be used in the reaction are a sodium salt, potassium salt and the like.

The reaction can be conducted in the absence of a solvent or in a solvent properly selected from dioxane, tetrahydrofuran, ethylether, n-hexane, cyclohexane, dichloromethane, chloroform, benzene, xylene, N,N-dimethylformamide, dimethylsulfoxide and the like.

(Scheme T)

The compound represented by the Formula (25) can be prepared by the reaction of 1 mol of the compound of the Formula (24) with the amino compound represented by $R^1NH_2$ or 1 to 2 mol of an ammonium salt at temperatures from a room temperature to 100° C. or approximately at a reflux temperature of the solvent for 1–24 hours. Examples of the amine to be used in the reaction are methylamine, ethylamine, n-propylamine, isopropylamine, n-butylamine, s-butylamine, t-butylamine and the like. Examples of the ammonium salts employed in the reaction are ammonium carbonate, ammonium acetate and the like. The reaction can be conducted in the absence of a solvent or in a solvent properly selected from dioxane, tetrahydrofuran, ethylether, n-hexane, cyclohexane, dichloromethane, chloroform, benzene, xylene, N,N-dimethylformamide, dimethylsulfoxide, water and the like.

(Scheme U)

The compound represented by the formula (26) can be prepared by the reaction of 1 mol of the compound of the formula (25) with about 1 mol of bromine at temperatures from an ice cold temperature to about 100° C. for 1–24 hours.

The reaction can be conducted in the absence of a solvent or in a solvent properly selected from dioxane, tetrahydrofuran, ethylether, n-hexane, cyclohexane, dichloromethane, chloroform, benzene, xylene, N,N-dimethylformamide, dimethylsulfoxide, methanol, ethanol, n-propanol, isopropanol and the like.

(Scheme V)

The compound (27) can be prepared by the reaction of 1 mol of the compound of the formula (26) with 1 mol to an excessive amount of chlorosulfonic acid at temperatures from an ice cold temperature to about 100° C. for 1–24 hours.

The reaction can be conducted in the absence of a solvent or in a solvent properly selected from dioxane, tetrahydrofuran, ethylether, n-hexane, cyclohexane, dichloromethane, chloroform and the like.

(Scheme W)

The compound represented by the formula (28) can be prepared by the reaction of the compound of the formula (27) with the amino compound represented by 1 to 2 mol of $R^7R^8NH$ or an ammonium salt at temperatures from a room temperature to about 100° C. for 1–24 hours.

Examples of the amine to be used in the reaction are ammonia, methylamine, ethylamine, n-propylamine, isopropylamine, n-butylamine, s-butylamine, t-butylamine, dimethylamine, dlethylamine, di-n-propylamine, diisopropylamine, di-n-butylamine, di-s-butylamine, di-t-butylamine and the like. Examples of the ammonium salt to be used in the reaction are an ammonium carbonate, ammonium acetate and the like.

The reaction can be conducted in the absence of a solvent or in a solvent properly selected from dioxane, tetrahydrofuran, ethylether, n-hexane, cyclohexane, dichloromethane, chloroform, benzene, xylene, N,N-dimethylformamide, dimethylsulfoxide, water and the like.

(Scheme X)

The compound represented by the formula (IB) can be prepared by the reaction of the compound of the formula (28) with 1 to 2 mol of the compound represented by the formula (29) and about the same molar amount of a base such as sodium carbonate in the presence of a catalyst at temperatures from a room temperature to 100° C. or approximately at a reflux temperature of the solvent for 1–24 hours.

The reaction can be conducted in a solvent properly selected from dioxane, tetrahydrofuran, ethylether, n-hexane, cyclohexane, dichloromethane, chloroform, benzene, xylene, N,N-dimethylformamide, dimethylsulfoxide, methanol, ethanol, n-propanol, isopropanol and the like. Examples of the catalyst to be used in the reaction are tetrakistriphenylphosphinepalladium, bistriphenylphosphinepalladium chloride, zinc chloride and the like.

(Scheme Y)

Finally, the compound (I) of the invention can be prepared by treating the compound of the formula (IB) in the same manner described in the Scheme F. Further, the compound (I) of the invention can alternatively be synthesized according to (Scheme Z) to (Scheme AA) shown in the following <Reaction Scheme 6>.

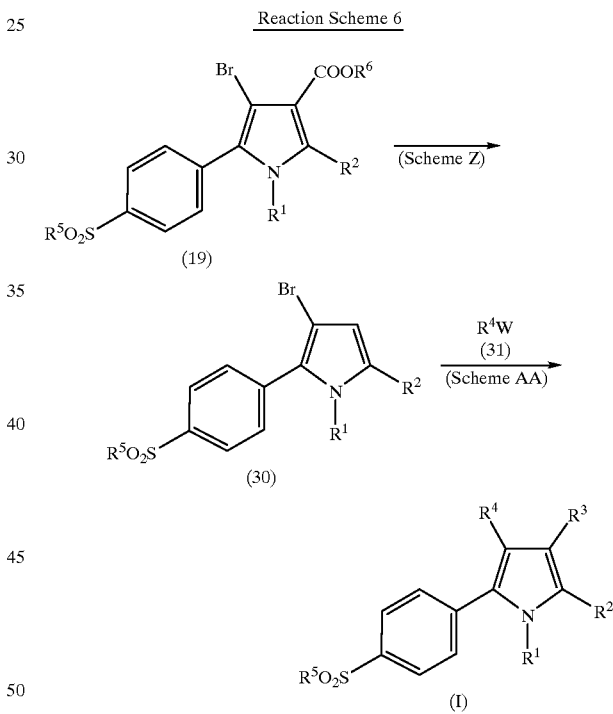

Reaction Scheme 6 wherein,
$R^1$, $R^2$, $R^3$, $R^4$, $R^5$ and $R^6$ are as defined above. W represents $B(OH)_2$ or $Sn(n\text{-}Bu)_3$.

(Scheme Z)

The compound (30) can be prepared by treating the compound (19) in the same manner as described in the Scheme F.

Examples of the acid to be used in the reaction are inorganic acids such as sulfuric acid, hydrochloric acid and nitric acid or organic acids such as acetic acid, citric acid, oxalic acid, lactic acid and butyric acid.

Examples of the base to be used in the reaction include alkali metal hydroxides such as lithium hydroxide, potassium hydroxide and sodium hydroxide, alkali metal carbonates such as sodium carbonate and potassium carbonate, alkali metal hydrogencarbonates such as sodium hydrogencarbonate and potassium hydrogencarbonate, alkali metal hydrides such as sodium hydride and potassium hydride, inorganic bases such as sodium and sodium amide, organic bases such as triethylamine, tri-n-butylamine, pyridine and N,N-dimethylaminopyridine or the like.

(Scheme AA)

The compound (I) of the invention can be prepared by the reaction of the compound (30) with 1–2 equivalents of the compound (31) and a base solution of 1 equivalent of a sodium carbonate in the presence of a catalyst at temperatures from a room temperature to 100° C. or approximately at a reflux temperature of the solvent for 1–24 hours.

The reaction can be conducted in a solvent properly selected from dioxane, tetrahydrofuran, diethylether, n-hexane, cyclohexane, dichloromethane, chloroform, benzene, xylene, N,N-dimethylformamide, dimethylsulfoxide, methanol, ethanol, n-propanol, isopropanol and the like. Examples of the catalyst to be used in the reaction are tetrakistriphenylphosphinepalladium, bistriphenylphosphinepalladium chloride, zinc chloride and the like.

The title compounds of the present invention can be administered orally and/or parenterally in accordance with the conventional dosage forms. The dosage forms may be, for example, tablets, dust formulations, granules, powers, capsules, liquids, emulsions, suspensions and injections, all of which are manufactured by conventional methods. In the case where the compounds are administered to human as an anti-inflammatory agent, antipyretic agent, analgesic agent, antirheumatic agent and antitumor agent, the dosage is normally 1–1000 mg per day, which will vary depending on the age, body weight, symptoms, route of administration, administration frequency and the like.

The compounds of the invention as active ingredient demonstrate a strong anti-inflammatory action, antipyretic action, analgesic action, antirheumatic action, cytostatic action and the like based on the COX-2 selective inhibitory action with minimal adverse side effects and enhanced safety. Therefore, the compound (I) of the invention is useful as anti-inflammatory agents, antipyretic agents, analgesic agents, antirheumatic agents and antitumor agents.

BEST MODE FOR CARRYING OUT THE INVENTION

The present invention will be described further in detail by the following preparation examples, examples, and test examples.

Preparation Example 1

4-(4-fluorophenyl)-2-methyl-5-(4-methylsulfonylphenyl)-1H-pyrrole

According to the Reaction Scheme 1, the compound of the preparation example 1 was prepared in the following procedure.

(1) 46.3 g (0.389 mol) of thionyl chloride was added to 15.0 g (0.097 mmol) of 4-fluorophenyl acetate and stirred at 80° C. for 1 hour, then concentrated under reduced pressure to obtain 4-fluorophenylacetyl chloride. 200 ml of methylene chloride solution containing 24.2 g of thioanisole (0.195 mol) was added to the obtained compound and then 15.6 g (0.117 mol) of an aluminum chloride was added thereto, then heated under reflux for 4 hours. 300 ml of IN hydrochloric acid was added dropwise to the reaction mixture which was then extracted with 500 ml of methylene chloride. The organic layer was washed with 500 ml of saturated sodium bicarbonate aqueous solution and 500 ml of saturated saline, then dried over anhydrous magnesium sulfate and concentrated under reduced pressure to obtain 18.0 g of 1-(4-fluorophenyl)-2-(4-methylthiophenyl)ethanone as yellow powdery crystal (yield: 53.2%).

Melting Point: 137–139° C.

1H-NMR(CDC13)δ: 7.90(2H,m,Ar-H), 7.26(2H,m,Ar-H), 7.21(2H,m,Ar-H), 7.00(2H,m,Ar-H), 4.21(2H,s,CH$_2$), 2.51(3H,s,SCH$_3$).

MASS (EI method): 260(M$^+$)

Elemental analysis for $C_{15}H_{13}FOS$

Calcd.(%) C; 69.21 H; 5.03

Found(%) C; 69.40 H; 4.90

(2) 17.0 g (0.065 mol) of 1-(4-fluorophenyl)-2-(4-methylthiophenyl)ethanone was dissolved in 100 ml of acetic acid and 51 ml of 33% hydrobromic acid in acetic acid solution was added thereto. Further, 10.4 g (0.065 mol) of bromine was added dropwise to the solution at room temperature for 5 minutes, then stirred at the room temperature for 15 minutes. After concentration under reduced pressure, 200 ml of methylene chloride was added thereto, then washed three times with 100 ml of saturated sodium bicarbonate aqueous solution and dried over anhydrous magnesium sulfate followed by concentration under reduced pressure to obtain 14.2 g of 1-bromo-1-(4-fluorophenyl)-2-(4-methylthiophenyl)ethanone of pale yellow powdery crystal (yield: 64.1%).

Melting Point: 109–112° C.

$^1$H-NMR(CDCl$_3$) δ: 7.89(2H,m,Ar-H), 7.52(2H,m,Ar-H), 7.26(2H,d,J=8.4 Hz,Ar-H), 7.06(2H,m,Ar-H), 6.30(1H,s,CH), 2.51(3H,s,SCH$_3$).

MASS (EI method): 399(M$^+$) and 260(M$^+$-Br)

Elemental Analysis for $C_{15}H_{12}BrFOS$

Calcd.(%) C; 53.11 H; 3.57

Found(%) C; 52.90 H; 3.70

(3) To 200 ml of N,N-dimethylformamide solution containing 20.0 g (0.059 mol) of 1-bromo-1-(4-fluorophenyl)-2-(4-methylthiophenyl)ethanone was added 18.0 g (0.118 mol) of ethyl 3-oxobutanate sodium salt, and stirred at room temperature for 2 hours, then stirred with heat at 60° C. for 4 hours. After concentration under reduced pressure, 200 ml of ethyl acetate was added and then washed with 100 ml of saturated saline for three times. The organic layer was dried over anhydrous magnesium sulfate, then concentrated under reduced pressure, followed by subjected to chromatography on silica gel (hexane:ethyl acetate=4:1) to obtain 20.0 g of 1-acetyl-2-(4-fluorophenyl)-3-(4-methylthiophenyl)-3-oxo-butylate as colorless oil (yield: 87.2%).

$^1$H-NMR(CDCl$_3$) δ: 7.84(2H,m,Ar-H), 7.27(2H,m,Ar-H), 7.19(2H,m,Ar-H), 6.96(2H,m,Ar-H), 5.30(1H,m,2-PhCHCH), 4.55(1H,m,CHCOO), 4.00(2H,m,OCH2CH3), 2.47,2.34(3H,ss,COCH$_3$), 2.17(3H,s,SCH$_3$), 1.25,1.19(3H,t t,OCH$_2$CH$_3$).

MASS (EI method): 388(M$^+$) and 343(M$^+$-OEt)

Elemental Analysis for $C_{21}H_{21}OF_4S$

Calcd.(%) C; 64.93 H; 5.45

Found(%) C; 65.10 H; 5.20

(4) 1.22 g (5.65 mmol) of 3-chloroperbenzoic acid was added to 30 ml of methylene chloride solution containing 1.0 g (2.57 mmol) of ethyl 1-acetyl-2-(4-fluorophenyl)-3-(4-methylthiopheny)-3-oxo-butylate and heated under reflux for 1 hour. The reaction mixture was washed with 50 ml of saturated sodium bicarbonate aqueous solution and 50 ml of saturated saline, then dried over anhydrous magnesium sulfate and concentrated under reduced pressure to obtain 1.0 g of ethyl 1-acetyl-2-(4-fluorophenyl)-3-(4-methylsulfonylphenyl)-3-oxo-butylate as white powdery crystal (yield: 92.5%).

$^1$H-NMR(CDCl$_3$) δ: 8.12(2H,m,Ar-H), 7.99(2H,m,Ar-H), 7.28(2H,m,Ar-H), 6.99(2H,m,Ar-H), 5.32(1H,m,PhCHCH), 4.60(1H,m,CHCOO), 4.05(2H,m,OCH$_2$CH$_3$), 3.03(3H,s, SO$_2$CH$_3$), 2.34,2.04(3H,s s,COCH$_3$), 1.23,1.07(3H,t t,OCH$_2$CH$_3$).

MASS (EI method): 420(M$^+$), 375(M$^+$-OEt) and 347(M$^+$ –COOEt)

Elemental Analysis for C$_{21}$H$_{21}$OF$_6$S

Calcd.(%) C; 59.99 H; 5.03

Found(%) C; 59.80 H; 4.90

(5) To 1.0 g (2.38mmol) of ethyl 1-acetyl-2-(4-fluorophenyl)-3-(4-methylsulfonylphenyl)-3-oxo-butylate, was added 1.24 g (4.76 mmol) of ammonium carbonate, and the mixture was heated at 100° C. for 30 minutes. 20 ml of purified water was added thereto and further heated at 120° C. for 15 minutes. The solution was cooled to room temperature and extracted with 100 ml of methylene chloride, which was washed with 100 ml of saturated saline, then dried over anhydrous magnesium sulfate and concentrated under reduced pressure. The resulting crystal was recrystalized from ethanol to obtain 0.7 g of ethyl (4-(4-fluorophenyl)-2-methyl-5-(4-methylsulfonylphenyl)-1H-pyrrole)-3-carboxylate as white powdery crystal (yield: 73.3%).

Melting Point: 219–221° C.

$^1$H-NMR(CDCl$_3$) δ: 8.34(1H,br-s,NH), 7.83(2H,d,J=8.4 Hz,Ar-H), 7.42(2H,d,J=8.4 Hz,Ar-H), 7.03(2H,m,Ar-H), 6.94(2H,m,Ar-H), 4.12(2H,q,J=8.0 Hz,7.2 Hz,6.8 Hz,OCH$_2$CH$_3$), 3.04(3H,s,SO$_2$CH$_3$), 2.61(3H,s,2–CH$_3$), 1.10(3H,t,OCH$_2$CH$_3$).

MASS (EI method): 401(M$^+$), 372(M$^+$-Et) and 356(M$^+$-OEt)

Elemental Analysis for C$_{21}$H$_{20}$FNO$_4$S

Calcd.(%) C; 62.83 H; 5.02 N; 3.49

Found(%) C; 62.70 H; 4.70 N; 3.70

(6) To 200 mg (0.498 mmol) of ethyl (4-(4-fluorophenyl)-2-methyl-5-(4-methylsulfonylphenyl)-1H-pyrrole)-3-carboxylate was added 5 ml of 80% sulfuric acid solution and stirred with heat at 80° C. for 15 minutes. 20 ml of purified water was added to the solution which was then extracted with ethyl acetate. The organic layer was dried over anhydrous magnesium sulfate and then concentrated under reduced pressure. Recrystallization was conducted using benzene/petroleum ether to obtain 145 mg of 4-(4-fluorophenyl)-2-methyl-5-(4-methylsulfonylphenyl)-1H-pyrrole as white plate-like crystal (yield: 88.4%).

Melting Point: 197–198° C.

$^1$H-NMR(CDCl$_3$) δ: 7.97(1H,br-s,NH), 7.75(2H,m,Ar-H), 7.43(2H,m,Ar-H), 7.26(2H,m,Ar-H), 7.01(2H,m,Ar-H), 6.12(1H,m,3–CH) 3.04(3H,s,SO$_2$CH$_3$), 2.34(3H,s,2–CH$_3$).

MASS (EI method): 329(M$^+$) and 250(M$^+$-SO$_2$Me)

Elemental Analysis for C$_{18}$H$_{16}$FNO$_2$S

Calcd.(%) C; 65.63 H; 4.90 N; 4.25

Found(%) C; 65.38 H; 4.95 N; 4.00

Each of the compounds of the Preparation Examples 1, 15, 50 and 51 was prepared according to the Reaction Scheme 1.

Each of the compounds of the Preparation Examples 2–14, 16, 17, 19, 25, 34 and 53 was prepared according to the Reaction Scheme 3.

Each of the compounds of the Preparation Examples 18, 20–24, 26–33, 35–39 and 52 was prepared according to the Reaction Scheme 4.

Each of the compounds of the Preparation Examples 40–45 was prepared according to the Reaction Scheme 5.

Each of the compounds of the Preparation Examples 46–49 was prepared according to the Reaction Scheme 6.

Preparation Example 2

4-(4-chlorophenyl)-2-methyl-5-(4-methylsulfonylphenyl)-1H-pyrrole $^1$H-NMR(CDCl$_3$) δ: 8.12(1H,br-s,NH), 7.80(2H,d,J=8.8 Hz,Ar-H), 7.42(2H,d,J=8.8 Hz,Ar-H), 7.26(4H,m,Ar-H), 6.07(1H,s,3–CH), 3.07(3H,s,SO$_2$CH$_3$), 2.37(3H,s,2–CH$_3$).

MASS (EI method): 346(M$^+$)

Elemental Analysis for C$_{18}$H$_{16}$ClNO$_2$S

Calcd.(%) C; 62.51 H; 4.66 N; 4.05

Found(%) C; 62.70 H; 4.80 N; 3.90

Preparation Example 3

4-(3-fluorophenyl)-2-methyl-5-(4-methylsulfonylphenyl)-1H-pyrrole $^1$H-NMR(CDCl$_3$) δ: 8.18(1H,br-s,NH), 7.80(2H,d,J=8.8 Hz,Ar-H), 7.44(2H,d,J=8.1 Hz,Ar-H), 7.24(1H,m,Ar-H), 7.07(1H,d,J=7.3 Hz,Ar-H), 7.01(1H,d,J=10.3 Hz,Ar-H), 6.93(1H,m,Ar-H), 6.09(1H,S,3–CH), 3.07(3H,s,SO$_2$CH$_3$), 2.37(3H,s,2–CH$_3$).

MASS (EI method): 329(M$^+$)

Elemental Analysis for C$_{18}$H$_{16}$FNO$_2$S

Calcd.(%) C; 65.63 H; 4.90 N; 4.25

Found(%) C; 65.38 H; 4.95 N; 4.00

Preparation Example 4

4-(3-chlorophenyl)-2-methyl-5-(4-methylsulfonylphenyl)-1H-pyrrole $^1$H-NMR(CDCl$_3$) δ: 8.24(1H,br-s,NH), 7.78(2H,d,J=8.1 Hz,Ar-H), 7.42(2H,d,J=8.8 Hz,Ar-H), 7.32(1H,s,Ar-H), 7.21(2H,m,Ar-H), 7.16(1H,m,Ar-H), 6.08(1H,s,3–CH), 3.07(3H,s,SO$_2$CH$_3$), 2.37(3H,s,2–CH$_3$).

MASS (EI method): 346(M$^+$)

Elemental Analysis for C$_{18}$H$_{16}$ClNO$_2$S

Calcd.(%) C; 62.51 H; 4.66 N; 4.05

Found(%) C; 62.20 H; 4.80 N; 4.30

Preparation Example 5

4-(-fluorophenyl)-2-methyl-5-(4-methylsulfonylphenyl)-1H-pyrrole $^1$H-NMR(CDCl$_3$) δ: 8.22(1H,br-s,NH), 7.78(2H,d,J=8.8 Hz,Ar-H), 7.38(2H,d,J=8.1 Hz,Ar-H), 7.26(2H,m,Ar-H), 7.10(2H,m,Ar-H), 6.13(1H,s,3–CH), 3.05(3H,s,SO$_2$CH$_3$), 2.39(3H,s,2–CH$_3$).

MASS (EI method): 329(M$^+$)

Elemental analysis for C$_{18}$H$_{16}$FNO$_2$S

Calcd.(%) C; 65.63 H; 4.90 N; 4.25

Found(%) C; 65.38 H; 4.95 N; 4.00

Preparation Example 6

4-(2-chlorophenyl)-2-methyl-5-(4-methylsulfonylphenyl)-1H-pyrrole $^1$H-NMR(CDCl$_3$) δ: 8.29(1H,br-s,NH), 7.72(2H,d,J=8.8 Hz,Ar-H), 7.45(1H,d,J=9.5 Hz,Ar-H), 7.25(5H,m,Ar-H), 6.08(1H,s,3–CH), 3.03(3H,s,SO$_2$CH$_3$), 2.40(3H,s,2–CH$_3$).

MASS (EI method): 346(M$^+$)

Elemental analysis for C$_{18}$H$_{16}$ClNO$_2$S

Calcd.(%) C; 62.51 H; 4.66 N; 4.05

Found(%) C; 62.30 H; 4.40 N; 4.10

Preparation Example 7

4-(2,4-difluorophenyl)-2-methyl-5-(4-methylsulfonylphenyl)-1H-pyrrole $^1$H-NMR(CDCl$_3$) δ: 8.20(1H,br-s,NH), 7.79(2H,d,J=8.8 Hz,Ar-H), 7.36(2H,d,J=8.1 Hz,Ar-H), 7.21(1H,m,Ar-H), 6.86(1H,d,J=8.1 Hz,Ar-H), 6.83(1H,d,J=8.8 Hz,Ar-H), 6.09(1H,s,3–CH), 3.06(3H,s,SO$_2$CH$_3$), 2.38(3H,s,2–CH$_3$).

MASS (EI method): 347(M$^+$)

Elemental analysis for C$_{18}$H$_{15}$F$_2$NO$_2$S

Calcd.(%) C; 62.24 H; 4.35 N; 4.03

Found(%) C; 62.30 H; 4.50 N; 3.80

Preparation Example 8

4-(3,4-difluorophenyl)-2-methyl-5-(4-methylsulfonylphenyl)-1H-pyrrole $^1$H-NMR(CDCl$_3$) δ: 8.11(1H,br-s,NH), 7.82(2H,d,J=8.1 Hz,Ar-H), 7.42(2H,d,J=8.8 Hz,Ar-H), 7.05(3H,m,Ar-H), 6.05(1H,s,3–CH), 3.08(3H,s,SO$_2$CH$_3$), 2.37(3H,s,2–CH$_3$).

MASS (EI method): 347(M$^+$)

Elemental analysis for C$_{18}$H$_5$F$_2$NO$_2$S

Calcd.(%) C; 62.24 H; 4.35 N; 4.03

Found(%) C; 62.40 H; 4.60 N; 4.10

Preparation Example 9

4-(2-chloro-4-fluorophenyl)-2-methyl-5-(4-methylsulfonylphenyl)-1H-pyrrole $^1$H-NMR(CDCl$_3$) δ: 8.21(1H,br-s,NH), 7.76(2H;d,J=8.1 Hz,Ar-H), 7.26(2H,d,J=8.1 Hz,Ar-H), 7.21(2H,m,Ar-H), 6.96(1H,m,Ar-H), 6.05(1H,s,3–CH), 3.04(3H,s,SO$_2$CH$_3$), 2.39(3H,s,2–CH$_3$).

MASS (EI method): 364(M$^+$)

Elemental analysis for C$_{18}$H$_{15}$ClFNO$_2$S

Calcd.(%) C; 59.42 H; 4.16 N; 5.22

Found(%) C; 59.10 H; 4.10 N; 5.30

Preparation Example 10

4-(3-chloro-4-fluorophenyl)-2-methyl-5-(4-methylsulfonylphenyl)-1H-pyrrole $^1$H-NMR(CDCl$_3$) δ: 8.53(1H,br-s,NH), 7.71(2H,d,J=8.1 Hz,Ar-H), 7.25(2H,d,J=8.8 Hz,Ar-H), 7.21(2H,m,Ar-H), 6.96(1H,m,Ar-H), 6.03(1H,s,3–CH$_3$), 3.04(3H,s,SO$_2$CH$_3$), 2.39(3H,s,2–CH$_3$).

MASS (EI method): 364(M$^+$)

Elemental analysis for C$_{18}$H$_{15}$FClNO$_2$S

Calcd.(%) C; 59.42 H; 4.16 N; 5.22

Found(%) C; 59.30 H; 4.20 N; 4.90

Preparation Example 11

2-ethyl-4-(4-fluorophenyl)-5-(4-methylsulfonylphenyl)-1H-pyrrole $^1$H-NMR(CDCl$_3$) δ: 8.17(1H,br-s,NH), 7.78(2H,d,J=8.8 Hz,Ar-H), 7.42(2H,d,J=8.8 Hz,Ar-H), 7.27(2H,dd,J=8.8 Hz,6.0 Hz,Ar-H), 7.00(2H,t,J=8.8 Hz,Ar-H), 6.09(1H,s,Ar-H), 3.06(3H,s,SO$_2$CH$_3$), 2.71(2H,q,J=7.2 Hz,2–CH$_2$CH$_3$), 1.33(3H,t,J=7.2 Hz,2–CH$_2$CH$_3$).

MASS (EI method): 343(M$^+$)

Elemental analysis for C$_{19}$H$_{18}$FNO$_2$S

Calcd.(%) C; 66.45 H; 5.28 N; 4.08

Found(%) C; 66.30 H; 5.10 N; 4.20

Preparation Example 12

4-(4-fluorophenyl)-5-(4-methylsulfonylphenyl)-2-n-propyl-1H-pyrrole $^1$H-NMR(CDCl$_3$) δ: 8.20(1H,br-s,NH), 7.79(2H,d,J=8.8 Hz,Ar-H), 7.42(2H,d,J=8.8 Hz,Ar-H), 7.27(2H,dd,J=8.8 Hz,6.0 Hz,Ar-H), 7.01(2H,t,J=8.8 Hz,Ar-H), 6.09(1H,s,Ar-H), 3.07(3H,s,SO$_2$CH$_3$), 2.71(2H,q,J=7.2 Hz,2–CH$_2$CH$_2$CH$_3$), 2.04(2H,m,2–CH$_2$CH$_2$CH$_3$), 1.35(3H,t,J=7.2 Hz,2–CH$_2$CH$_2$CH$_3$).

MASS (EI method): 357(M$^{30}$)

Elemental analysis for C$_{20}$H$_{20}$FNO$_2$S

Calcd.(%) C; 67.20 H; 5.64 N; 3.92

Found(%) C; 67.30 H; 5.50 N; 4.20

Preparation Example 13

4-(4-fluorophenyl)-2-isopropyl-5-(4-methylsulfonylphenyl)-1H-pyrrole $^1$H-NMR(CDCl$_3$) δ: 8.19(1H,br-s,NH), 7.79(2H,d,J=8.8 Hz,Ar-H), 7.43(2H,d,J=8.8 Hz,Ar-H), 7.29(2H,dd,J=8.8 Hz,6.0 Hz,Ar-H), 6.99(2H,t,J=8.8 Hz,Ar-H), 6.11(1H,s,Ar-H), 3.06(3H,s,SO$_2$CH$_3$), 2.90(1H,m,2–CH(CH$_3$)$_2$), 1.40(6H,m,2–CH(CH$_3$)$_2$).

MASS (EI method): 357(M$^+$)

Elemental analysis for C$_{20}$H$_{20}$FNO$_2$S

Calcd.(%) C; 67.20 H; 5.64 N; 3.92

Found(%) C; 67.40 H; 5.60 N; 4.10

Preparation Example 14

2-t-butyl-4-(4-fluorophenyl)-5-(4-methylsulfonylphenyl)-1H-pyrrole $^1$H-NMR(CDCl$_3$)δ: 8.07(1H,br-s,NH), 7.80(2H,d,J=8.8 Hz,Ar-H), 7.44(2H,d,Ar-H), 7.28(2H,dd,J=7.2 Hz,8.0 Hz,Ar-H), 7.00(2H,t,J=8.8 Hz,Ar-H), 6.10(1H,s,Ar-H), 3.07(3H,s,SO$_2$CH$_3$), 1.38(9H,s,t-Bu).

MASS (EI method): 371(M$^+$)

Elemental analysis for C$_{21}$H$_{22}$FNO$_2$S

Calcd.(%) C; 67.90 H; 5.97 N; 3.77

Found(%) C; 67.80 H; 6.00 N; 4.00

Preparation Example 15

1,2-dimethyl-4-(4-fluorophenyl)-5-(4-methylsulfonylphenyl)-1H-pyrrole $^1$H-NMR(CDCl$_3$) δ: 7.91(2H,m,Ar-H), 7.42(2H,d,Ar-H), 7.04(2H,m,Ar-H), 6.90(2H,t,J=8.8 Hz,Ar-H), 6.14(1H,s,3–CH), 3.44(3H,s,N–CH$_3$), 3.12(3H,s,SO$_2$CH$_3$), 2.34(3H,s,2–CH$_3$)

MASS (EI method): 343(M$^3$)

Elemental analysis for C$_{19}$H$_{18}$FNO$_2$S

Calcd.(%) C; 66.45 H; 5.28 N; 4.08

Found(%) C; 66.60 H; 5.00 N; 4.20

Preparation Example 16

4-(4-methoxyphenyl)-2-methyl-5-(4-methylsulfonylphenyl)-1H-pyrrole (1) 14.3 g (0.12 mol) of thionyl chloride was added to 5.0 g (30.1 mmol) of 4-methoxyphenyl acetatic acid and stirred at 8° C. for 1 hour, then concentrated under reduced pressure to obtain a 4-methoxyphenyl acetyl chloride. To the obtained compound, 200 ml of methylene chloride solution containing 7.5 g (0.195 mol) of thioanisole and, subsequently. 4.82 g (36.1 mol) of aluminium chloride was added, then heated under reflux for 4 hours. 100 ml of 1N hydrochloric acid was added dropwise to the reaction mixture which was then extracted with 100 ml of methylene chloride. The organic layer was washed with 100 ml of saturated sodium bicarbonate aqueous solution and 100 ml of saturated saline, then dried over anhydrous magnesium sulfate and concentrated under reduced pressure followed by recrystalization from ethanol/hexane to obtain 5.81 g of 1-(4-fluorophenyl)-2-(4-methylthiophenyl)ethanone as white powdery crystal (yield: 71%).

Melting point: 123.5–124.5° C.
$^1$H-NMR(CDCl$_3$) δ: 7.96(2H,d,J=7.2 Hz,Ar-H), 7.30(2H, d,J=8.4 Hz,Ar-H), 7.22(2H,d,J=8.4 Hz,Ar-H), 6.91(2H,d,J= 8.4 Hz,Ar-H), 4.22(2H,s,CH$_2$), 3.84(3H,s,OCH$_3$), 2.57(3H, s,SCH$_3$).
MASS (EI method): 272(M$^+$)
Elemental analysis for C$_{16}$H$_{16}$O$_2$S
Calcd.(%) C; 70.56 H; 5.92
Found(%) C; 70.48 H; 6.01

(2) 0.44g (11.0 mol) of 60% sodium hydride was added to 27 ml of N,N-dimethylformamide solution containing 2.72 g (10.0 mmol) of 1-(4-methoxyphenyl)-2-(4-methylthiophenyl)ethanone, and stirred at the room temperature for 30 minutes, then 1.51 g (11.0 mol) of bromoacetone was added and further stirred at room temperature for 1 hour. 400 ml of ethyl acetate was added thereto and the mixture was washed three times with 200 ml of saturated saline. The organic layer was dried over anhydrous magnesium sulfate, then concentrated under reduced pressure followed by subjected to chromatography on silica gel (hexane:ethyl acetate=4:1) to obtain 2.27 g of 2-(4-methoxyphenyl)-1-(4-methylthiophenyl)butane-1,3-dion as colorless oil (yield: 69%).

Melting Point: 74–75° C.
$^1$H-NMR(CDCl$_3$) δ: 7.86(2H,d,J=8.8 Hz,Ar-H), 7.17(2H, d,J=8.8 Hz,Ar-H), 7.15(2H,d,J=8.8 Hz,Ar-H), 6.80(2H,d,J= 8.8 Hz,Ar-H), 5.00(1H,m,CHCH$_2$), 3.74(3H,s,OCH$_3$), 3.54 (1H,dd,J=18.0, 9.6 Hz,CHCH$_2$), 2.72(1H,d,J=18.0 Hz,CHCH$_2$), 2.47(3H,s,SCH$_3$), 2.18(3H,s,COCH$_3$).
MASS (EI method): 328(M$^+$)
Elemental analysis for C$_{19}$H$_{20}$O$_3$S
Calcd.(%) C; 69.49 H; 6.14
Found(%) C; 69.22 H; 5.96

(3) To 13 ml of methylene chloride solution containing 1.31 g (4 mmol) of 2-(4-methoxyphenyl)-1-(4-methylthiophenyl)butane-1,3-dion was added 2.1 g (8.5 mmol) of 70% 3-chloroperbenzoic acid and heated under reflux for 1 hour. The reaction mixture was washed with 20 ml of saturated sodium bicarbonate aqueous solution and 20 ml of saturated saline, then dried over anhydrous magnesium sulfate and concentrated under reduced pressure to obtain a mixture of 2-(4-methoxyphenyl)-1-(4-methylsulfonylphenyl)butane-1,3-dion as pale yellow oil.

$^1$H-NMR(CDCl$_3$) δ: 8.09(2H,d,J=8.8 Hz,Ar-H), 7.95(2H, d,J=8.8 Hz,Ar-H), 7.14(2H,d,J=8.8 Hz,Ar-H), 6.82(2H,d,J= 8.8 Hz,Ar-H), 5.00(1H,dd,J=10.4, 3.6 Hz, CHCH$_2$), 3.75 (3H,s,OCH$_3$), 3.60(1H,dd,J=18.0, 10.4 Hz,CHCH$_2$), 3.03 (3H,s,SO$_2$CH$_3$), 2.78(1H,dd,J=18.0 Hz, 3.6 Hz,CHCH$_2$), 2.20(3H,s,COCH$_3$).
MASS (EI method): 360(M$^+$)
Elemental analysis for C$_{19}$H$_{20}$O$_5$S
Calcd.(%) C; 63.32 H; 5.59
Found(%) C; 63.05 H; 5.71

(4) 0.5 g (6.5 mmol) of ammonium acetate was added to an acetic acid solution containing the mixture obtained in (3) and heated at 100° C. for 30 minutes. The reaction mixture was concentration under reduced pressure, and then extracted with methylene chloride, which was washed with 20 ml of saturated sodium bicarbonate aqueous solution and 20 ml of saturated saline, then dried over anhydrous magnesium sulfate and concentrated under reduced pressure.

The resulting crystal was recrystalized from ethanol to obtain 0.95 g of 4-(4-methoxyphenyl)-2-methyl-5-(4-methylsulfonylphenyl)-1H-pyrrole as white powdery crystal (yield: 70%).

Melting Point: 100–101° C.
$^1$H-NMR(CDCl$_3$) δ: 8.10(1H,br-s,NH), 7.70(2H,d,J=8.4 Hz,Ar-H), 7.43(2H,d,J=8.4 Hz,Ar-H), 7.23(2H,d,J=8.8 Hz,Ar-H), 6.85(2H,d,J=8.8,Ar-H), 6.06(1H,m,3-H), 3.83 (3H,s,OCH$_3$), 3.06(3H,s,SO$_2$CH$_3$), 2.36(3H,s,2–CH$_3$).
MASS (EI method): 341(M$^+$)
Elemental analysis for C$_{19}$H$_{19}$NO$_3$S
Calcd.(%) C; 66.84 H; 5.61 N; 4.10
Found(%) C; 66.79 H; 5.55 N; 3.89

Preparation Example 17

4-(4-methylphenyl)-2-methyl-5-(4-methylsulfonylphenyl)-1H-pyrrole
$^1$H-NMR(CDCl$_3$) δ: 8.10(1H,br-s,NH), 7.77(2H,d,J=8.1 Hz,Ar-H), 7.44(2H,d,J=8.1 Hz,Ar-H), 7.21(2H,d,J=8.8 Hz,Ar-H), 7.12(2H,d,J=8.8 Hz,Ar-H), 6.08(1H,d,J=1.5 Hz,3–CH), 3.06(3H,s,SO$_2$CH$_3$), 2.37(3H,s,2–CH$_3$), 2.35 (3H,s,Ar–CH$_3$).
MASS (EI method): 325(M$^+$)
Elemental analysis for C$_{19}$H$_{19}$NO$_2$S
Calcd.(%) C; 70.13 H; 5.88 N; 4.30
Found(%) C; 69.85 H; 5.65 N; 4.01

Preparation Example 18

4-(4-methylthiophenyl)-2-methyl-5-(4-methylsulfonylphenyl)-1H-pyrrole
$^1$H-NMR(CDCl$_3$) δ: 8.23(1H,br-s,NH), 7.76(2H,d,J=8.8 Hz,Ar-H), 7.44(2H,d,J=8.8 Hz,Ar-H), 7.23(2H,d,J=8.8 Hz,Ar-H), 7.19(2H,d,J=8.8 Hz,Ar-H), 6.07(1H,s,3–CH), 3.05(3H,s,SO$_2$CH$_3$), 2.50(3H,s,SCH$_3$), 2.36(3H,s,2–CH$_3$).
MASS (EI method): 357(M$^+$)
Elemental analysis for C$_{19}$H$_{19}$NO$_2$S$_2$
Calcd.(%) C; 63.84 H; 5.36 N; 3.92
Found(%) C; 63.55 H; 5.61 N; 4.06

Preparation Example 19

4-(4-dimethylaminophenyl)-2-methyl-5-(4-methylsulfonylphenyl)-1H-pyrrole
$^1$H-NMR(CDCl$_3$) δ: 8.10(1H,br-s,NH), 7.75(2H;d,J=7.3 Hz,Ar-H), 7.47(2H,d,J=8.8 Hz,Ar-H), 7.19(2H,d,J=8.8 Hz,Ar-H), 6.69(2H,d,J=8.1 Hz,Ar-H), 6.05(1H,s,3–CH), 3.05(3H,s,SO$_2$CH$_3$), 2.96(6H,s,NCH$_3$×2), 2.35(3H,s, 2–CH$_3$).
MASS (EI method): 354(M$^+$)
Elemental analysis for C$_{20}$H$_{22}$N$_2$O$_2$
Calcd.(%) C; 67.77 H; 6.26 N; 7.90
Found(%) C: 67.58 H; 6.03 N; 8.00

Preparation Example 20

4-(3-methoxyphenyl)-2-methyl-5-(4-methylsulfonylphenyl)-1H-pyrrole
$^1$H-NMR(CDCl$_3$) δ: 8.10(1H,br-s,NH), 7.79(2H,d,J=8.0 Hz,Ar-H), 7.45(2H,d,J=8.8 Hz,Ar-H), 7.22(1H,d,J=8.1 Hz,Ar-H), 6.89(1H,d,J=7.3 Hz,Ar-H), 6.88(1H,s,Ar-H), 6.81(1H,d,J=7.3 Hz,Ar-H), 6.10(1H,s,3–CH), 3.76(3H,s, OCH$_3$), 3.06(3H,s,SO$_2$CH$_3$), 2.37(3H,s,2–CH$_3$).
MASS (EI method): 341(M$^+$)
Elemental analysis for C$_{19}$H$_{19}$NO$_3$
Calcd.(%) C; 66.84 H; 5.61 N; 4.10

Found(%) C; 66.98 H; 5.41 N; 4.22

Preparation Example 21

4-(3-methylphenyl)-2-methyl-5-(4-methylsulfonylphenyl)-1H-pyrrole $^1$H-NMR(CDCl$_3$) δ: 8.11(1H,br-s,NH), 7.77(2H,d,J=8.8 Hz,Ar-H), 7.44(2H,d,J=8.8 Hz,Ar-H), 7.18(2H,m,Ar-H), 7.08(2H,m,Ar-H), 6.09(1H,d,J=2.8 Hz,3–CH), 3.06(3H,s,SO$_2$CH$_3$), 2.37(3H,s,2–CH$_3$), 2.32(3H,s,Ar–CH$_3$).

MASS (EI method): 325(M$^+$)
Elemental analysis for C$_{19}$H$_{19}$NO$_2$
Calcd.(%) C; 70.13 H; 5.88 N; 4.30
Found(%) C; 69.95 H; 5.65 N; 4.05

Preparation Example 22

4-(3-methylthiophenyl)-2-methyl-5-(4-methylsulfonylphenyl)-1H-pyrrole $^1$H-NMR(CDCl$_3$) δ: 8.10(1H,br-s,NH), 7.79(2H,d,J=8.3 Hz,Ar-H), 7.44(2H,d,J=8.3 Hz,Ar-H), 7.20(2H,m,Ar-H), 7.13(1H,d,J=7.8 Hz,Ar-H), 7.06(1H,d,J=7.8 Hz,Ar-H), 6.11(1H,s,3–CH), 3.06(3H,s,SO$_2$CH$_3$), 2.41(3H,s,SCH$_3$), 2.37(3H,s,2–CH$_3$).

MASS (EI method): 357(M$^+$)
Elemental analysis for C$_{19}$H$_{19}$NO$_2$S$_2$
Calcd.(%) C; 63.84 H; 5.36 N; 3.92
Found(%) C; 63.67 H; 5.30 N; 3.94

Preparation Example 23

4-(3-dimethylaminophenyl)-2-methyl-5-(4-methylsulfonylphenyl)-1H-pyrrole $^1$H-NMR(CDCl$_3$) δ: 8.19(1H,br-s,NH), 7.75(2H,d,J=8.8 Hz,Ar-H), 7.47(2H,d,J=8.1 Hz,Ar-H), 7.18(1H,t,J=8.1 Hz,Ar-H), 6.67(3h,m,Ar-H), 6.12(1H,s,3–CH), 3.04(3H,s,SO$_2$CH$_3$), 2.89(6H,s,NCH$_3$×2), 2.37(3H,s,2–CH$_3$).

MASS (EI method): 354(M$^+$)
Elemental analysis for C$_{20}$H$_{22}$N$_2$O$_2$S
Calcd.(%) C; 67.77 H; 6.26 N; 7.90
Found(%) C; 67.78 H; 6.30 N; 7.78

Preparation Example 24

4-(4-N-methylaminophenyl)-2-methyl-5-(4-methylsulfonylphenyl)-1H-pyrrole $^1$H-NMR(CDCl$_3$) δ: 8.02(1H,br-s,NH), 7.78(2H,d,J=8.1 Hz,Ar-H), 7.46(2H,d,J=8.1 Hz,Ar-H), 7.16(2H,d,J=8.1 Hz,Ar-H), 6.64(2H,m,NH and Ar-H), 6.04(1H,s,3–CH), 3.06(3H,s,SO$_2$CH$_3$), 2.87(3H,s,NCH$_3$), 2.36(3H,s,2–CH$_3$).

MASS (EI method): 340(M$^+$)
Elemental analysis for C$_{19}$H$_{20}$N$_2$O$_2$S
Calcd.(%) C; 67.03 H; 5.92 N; 8.23
Found(%) C; 66.98 H; 6.21 N; 8.02

Preparation Example 25

4-(4-aminophenyl)-2-methyl-5-(4-methylsulfonylphenyl)-1H-pyrrole $^1$H-NMR(CDCl$_3$+CD$_3$OD) δ: 9.79(1H,br-s,NH), 7.76(2H,d,J=8.1 Hz,Ar-H), 7.47(2H,d,J=8.8 Hz,Ar-H), 7.29(2H,d,J=8.1 Hz,Ar-H), 7.10(2H,d,J=8.1 Hz, Ar-H), 6.03(1H,s,3–CH), 3.09(3H,s,SO$_2$CH$_3$), 2.35(3H,s,2–CH$_3$).

MASS (EI method): 326(M$^+$)
Elemental analysis for C$_{18}$H$_{18}$N$_2$O$_2$S
Calcd.(%) C; 66.23 H; 5.56 N; 8.58
Found(%) C; 66.44 H; 5.49 N; 8.60

Preparation Example 26

4-(4-N,N-diethylaminophenyl)-2-methyl-5-(4-methylsulfonylphenyl)-1H-pyrrole $^1$H-NMR(DMSO) δ: 10.98(1H,br-s,NH), 7.73(2H,d,J=8.8 Hz,Ar-H), 7.53(2H,d,J=8.8 Hz,Ar-H), 7.04(2H,d,J=8.8 Hz,Ar-H), 6.61(2H,d,J=8.8 Hz,Ar-H), 5.85(1H,s,3–CH), 3.29-3.33(4H,m,CH$_2$CH$_3$), 3.18(3H,s,SO$_2$CH$_3$), 2.25(3H,s,2–CH$_3$), 1.09(6H,t,J=7.2 Hz,CH$_2$CH$_3$).

MASS (EI method): 382(M$^+$)
Elemental analysis for C$_{22}$H$_{26}$N$_2$O$_2$S
Calcd.(%) C; 69.08 H; 6.85 N; 7.32
Found(%) C; 68.80 H; 6.69 N; 7.12

Preparation Example 27

4-(3-fluoro-4-methoxyphenyl)-2-methyl-5-(4-methylsulfonylphenyl)-1H-pyrrole $^1$H-NMR(CDCl$_3$) δ: 8.14(1H,br-s,NH), 7.79(2H,d,J=8.4 Hz,Ar-H), 7.43(2H,d,J=8.4 Hz,Ar-H), 7.04(1H,d,J=12.4 Hz,Ar-H), 7.00(1H,d,J=9.6 Hz,Ar-H), 6.92(1H,t,J=8.8 Hz,Ar-H), 6.04(1H,s,3–CH), 3.91(3H,s,OCH$_3$), 3.07(3H,s,SO$_2$CH$_3$), 2.36(3H,s,2–CH$_3$).

MASS (EI method): 359(M$^+$)
Elemental analysis for C$_{19}$H$_{18}$FNO$_3$S
Calcd.(%) C; 63.49 H; 5.05 N; 3.90
Found(%) C; 63.22 H; 4.96 N; 3.70

Preparation Example 28

4-(3-chloro-4-methoxyphenyl)-2-methyl-5-(4-methylsulfonylphenyl)-1H-pyrrole $^1$H-NMR(CDCl$_3$) δ: 8.15(1H,br-s,NH), 7.79(2H,d,J=8.1 Hz,Ar-H), 7.42(2H,d,J=8.8 Hz,Ar-H), 7.34(1H,d,J=2.2 Hz,Ar-H), 7.12(1H,dd,J=2.2 and 8.8 Hz,Ar-H), 6.86(1H,d,J=8.1 Hz,Ar-H), 6.04(1H,s,3–CH), 3.91(3H,s,OCH$_3$), 3.06(3H,s,SO$_2$CH$_3$), 2.36(3H,s,2–CH$_3$).

MASS (EI method): 375, 377(M$^+$)
Elemental analysis for C$_{19}$H$_{18}$ClNO$_3$S
Calcd.(%) C; 60.72 H; 4.83 N; 3.73
Found(%) C; 60.61 H; 4.85 N; 3.55

Preparation Example 29

4-(3,4-dimethoxyphenyl)-2-methyl-5-(4-methylsulfonylphenyl)-1H-pyrrole $^1$H-NMR(CDCl$_3$) δ: 8.44(1H,br-s,NH), 7.73(2H,d,J=8.1 Hz,Ar-H), 7.44(2H,d,J=7.3 Hz,Ar-H), 6.84(3H,m,Ar-H), 6.07(1H,s,3–CH), 3.89(3H,s,OCH$_3$), 3.76(3H,s,OCH$_3$), 3.04(3H,s,SO$_2$CH$_3$), 2.37(3H,s,2–CH$_3$).

MASS (EI method): 371(M$^+$)
Elemental analysis for C$_{20}$H$_{21}$NO$_4$S
Calcd.(%) C; 64.67 H; 5.70 N; 3.77
Found(%) C; 64.71 H; 5.70 N; 3.76

Preparation Example 30

4-(3,4-methylenedioxyphenyl)-2-methyl-5-(4-methylsulfonylphenyl)-1H-pyrrole $^1$H-NMR(CDCl$_3$) δ: 8.07(1H,br-s,NH), 7.79(2H,d,J=8.8 Hz,Ar-H), 7.44(2H,d,J=8.8 Hz,Ar-H), 6.78(3H,s,Ar-H), 6.04(1H,s,3–CH), 5.97(2H,s,—OCH$_2$O—), 3.06(3H,s,SO$_2$CH$_3$), 2.36(3H,s,2–CH$_3$).

MASS (EI method): 355(M$^+$)
Elemental analysis for C$_{19}$H$_{17}$NO$_4$S
Calcd.(%) C; 64.21 H; 4.82 N; 3.94
Found(%) C; 64.20 H; 4.98 N; 3.99

Preparation Example 31

4-(4-fluoro-3-methylphenyl)-2-methyl-5-(4-methylsulfonylphenyl)-1H-pyrrole $^1$H-NMR(CDCl$_3$) δ: 8.08(1H,br-s,NH), 7.79(2H,d,J=8.8 Hz,Ar-H), 7.42(2H,d,J=8.8 Hz,Ar-H), 7.14(1H,d,J=7.3 Hz,Ar-H), 7.05(1H,m,Ar-H), 6.92(1H,t,J=8.8 Hz,Ar-H), 6.05(1H,s,3–CH), 3.06(3H,s,SO$_2$CH$_3$), 2.37(3H,s,2–CH$_3$), 2.24(3H,s,Ar–CH$_3$).

MASS (EI method): 343(M$^+$)
Elemental analysis for C$_{19}$H$_{18}$FNO$_2$S
Calcd.(%) C; 66.45 H; 5.28 N; 4.08
Found(%) C; 66.20 H; 5.08 N; 4.00

Preparation Example 32

4-(4-N,N-dimethylamino-3-methylphenyl)-2-methyl-5-(4-methylsulfonylphenyl)-1H-pyrrole $^1$H-NMR(DMSO) δ: 10.9(1H,br-s,NH), 7.73(2H,d,J=8.8 Hz,Ar-H), 7.51(2H,d,J=8.8 Hz,Ar-H), 7.06(1H,bs,Ar-H), 6.99(1H,d,J=8.3 Hz,Ar-H), 6.94(1H,d,J=8.3,Ar-H), 5.89 (1H,d,J=1.5 Hz,3–CH), 3.16(3H,s,SO$_2$CH$_3$), 2.64(6H,s, NCH$_3$×2), 2.26(3H,s,2–CH$_3$), 2.22(3H,s,Ar–CH$_3$).

MASS (EI method): 368(M$^+$)
Elemental analysis for C$_{21}$H$_{24}$N$_2$O$_2$S
Calcd.(%) C; 68.45 H; 6.56 N; 7.60
Found(%) C; 68.49 H; 6.49 N; 7.61

Preparation Example 33

4-(3-chloro-4-N,N-dimethylaminophenyl)-2-methyl-5-(4-methylsulfonylphenyl)-1H-pyrrole $^1$H-NMR(CDCl$_3$) δ: 8.17(1H,br-s,NH), 7.80(2H,d,J=8.8 Hz,Ar-H), 7.45(2H,d,J=8.8 Hz,Ar-H), 7.35(1H,s,Ar-H), 7.11(2H,m,Ar-H), 6.06(1H,s,3–CH), 3.08(3H,s,SO$_2$CH$_3$), 2.88(6H,br-s,NCH$_3$×2), 2.36(3H,s,2–CH$_3$).

MASS (EI method): 388, 390(M$^+$)
Elemental analysis for C$_{20}$H$_{21}$ClN$_2$O$_2$S
Calcd.(%) C; 61.77 H; 5.44 N; 7.20
Found(%) C; 61.75 H; 5.49 N; 6.95

Preparation Example 34

4-(4-nitrophenyl)-2-methyl-5-(4-methylsulfonylphenyl)-1H-pyrrole $^1$H-NMR(CDCl$_3$) δ: 8.31(1H,br-s,NH), 8.14(2H,d,J=8.8 Hz,Ar-H), 7.84(2H,d,J=8.8 Hz,Ar-H), 7.45(2H,d,J=8.1 Hz,Ar-H), 7.44(2H,d,J=8.8 Hz,Ar-H), 6.17(1H,s,3–CH), 3.09(3H,s,SO$_2$CH$_3$), 2.39(3H,s,2–CH$_3$).

MASS (EI method): 356(M$^+$)
Elemental analysis. for C$_{18}$H$_{16}$N$_2$O$_4$S
Calcd.(%) C; 60.66 H; 4.52 N; 7.86
Found(%) C; 60.38 H; 4.67 N; 7.58

Preparation Example 35

4-(4-cyanophenyl)-2-methyl-5-(4-methylsulfonylphenyl)-1H-pyrrole $^1$H-NMR(CDCl$_3$) δ: 8.19(1H,br-s,NH), 7.84(2H,d,J=8.8 Hz,Ar-H), 7.56(2H,d,J=8.1 Hz,Ar-H), 7.43(2H,d,J=8.1 Hz,Ar-H), 7.40(2H,d,J=8.8 Hz,Ar-H), 6.13(1H,s,3–CH), 3.08(3H,s,SO$_2$CH$_3$), 2.38(3H,s,2–CH$_3$).

MASS (EI method): 336(M$^+$)
Elemental analysis for C$_{19}$H$_{16}$N$_2$O$_2$S
Calcd.(%) C; 67.84 H; 4.79 N; 8.33
Found(%) C; 67.60 H; 4.78 N; 8.30

Preparation Example 36

4-(4-trifluoromethylphenyl)-2-methyl-5-(4-methylsulfonylphenyl)-1H-pyrrole $^1$H-NMR(CDCl$_3$) δ: 8.19(1H,br-s,NH), 7.82(2H,d,J=8.8 Hz,Ar-H), 7.54(2H,d,J=8.8 Hz,Ar-H), 7.43(2H,d,J=8.1 Hz,Ar-H), 7.41(2H,d,J=8.8 Hz,Ar-H), 6.12(1H,s,3–CH), 3.08(3H,s,SO$_2$CH$_3$), 2.38(3H,s,2–CH$_3$).

MASS (EI method): 379(M$^+$)
Elemental analysis for C$_{19}$H$_{16}$F$_3$NO$_2$S
Calcd.(%) C; 60.15 H; 4.25 N; 3.69
Found(%) C; 60.39 H; 3.98 N; 3.65

Preparation Example 37

4-(5-N-methylindolyl)-2-methyl-5-(4-methylsulfonylphenyl)-1H-pyrrole $^1$H-NMR(CDCl$_3$) δ: 8.08(1H,br-s,NH), 7.72(2H,d,J=8.4 Hz,Ar-H), 7.59(1H,s,Ar-H), 7.43(2H,d,J=8.4 Hz,Ar-H), 7.36(1H,s,Ar-H), 7.25–7.27(1H,m,Ar-H), 7.15(1H,d,J=8.4 Hz,Ar-H), 7.05(1H,s,Ar-H), 6.44(1H,s,Ar-H), 6.13(1H,s, 3–CH), 3.81(3H,s,NCH$_3$), 3.02(3H,s,SO$_2$CH$_3$), 2.39(3H,s, 2–CH$_3$).

MASS (EI method): 364(M$^+$)
Elemental analysis for C$_{21}$H$_{20}$N$_2$O$_2$S
Calcd.(%) C; 69.21 H; 5.53 N; 7.69
Found(%) C; 68.95 H; 5.40 N; 7.72

Preparation Example 38

4-(6-N-methylindolyl)-2-methyl-5-(4-methylsulfonylphenyl)-1H-pyrrole $^1$H-NMR(CDCl$_3$) δ: 8.11(1H,br-s,NH), 7.74(2H,d,J=8.8 Hz,Ar-H), 7.53(1H,d,J=7.3 Hz,Ar-H), 7.45(2H,d,J=8.8 Hz,Ar-H), 7.30(1H,s,Ar-H), 7.05(2H,m,Ar-H), 6.47(1H,d, J=3.9 Hz,Ar-H), 6.15(1H,d,J=2.0 Hz,3–CH), 3.73(3H,s, SO$_2$CH$_3$), 3.04(3H,s,NCH$_3$), 2.40(3H,s,2–CH$_3$).

MASS (EI method): 364(M$^+$)
Elemental analysis for C$_{21}$H$_{20}$N$_2$O$_2$S
Calcd.(%) C; 69.21 H; 5.53 N; 7.69
Found(%) C; 69.46 H; 5.50 N; 7.55

Preparation Example 39

4-(5-2,3-dihydrobenzofuran)-2-methyl-5-(4-methylsulfonylphenyl)-1H-pyrrole $^1$H-NMR(CDCl$_3$) δ: 8.10(1H,br-s,NH), 7.76(2H,d,J=8.8 Hz,Ar-H), 7.44(2H,d,J=8.8 Hz,Ar-H), 7.14(1H,br-s,Ar-H), 7.05(1H,d,J=8.4 Hz,Ar-H), 6.73(1H,d,J=8.4 Hz,Ar-H), 6.04 (1H,s,3–CH), 4.59(2H,t,J=8.8 Hz,OCH$_2$CH$_2$), 4.19(2H,t,J= 8.8 Hz,OCH$_2$CH$_2$), 3.06(3H,s,SO$_2$CH$_3$), 2.36(3H,s,2–CH$_3$).

MASS (EI method): 353(M$^+$)
Elemental analysis for C$_{19}$H$_{19}$NO$_2$S
Calcd.(%) C; 67.97 H; 5.42 N; 3.96
Found(%) C; 70.05 H; 5.53 N; 4.03

Preparation Example 40

4-(4-methoxyphenyl)-2-methyl-5-(4-aminosulfonylphenyl)-1H-pyrrole $^1$H-NMR(CDCl$_3$+CD$_3$OD) δ: 7.74(2H,d,J=8.8 Hz,Ar-H), 7.40(2H,d,J=8.8 Hz,Ar-H), 7.23(2H,d,J=8.8 Hz,Ar-H), 6.84 (2H,d,J=8.8 Hz,Ar-H), 3.82(3H,s,OCH$_3$), 2.35(3H,s, 2–CH$_3$).

MASS (EI method): 342, 327(M$^+$)
Elemental analysis for C$_{18}$H$_{18}$N$_2$O$_3$S
Calcd.(%) C; 63.14 H; 5.30 N; 8.18
Found(%) C; 62.94 H; 5.53 N; 8.26

Preparation Example 41

4-(4-methylphenyl)-2-methyl-5-(4-aminosulfonylphenyl)-1H-pyrrole

1H-NMR(CDCl₃+CD₃OD) δ: 7.73(2H,d,J=8.8 Hz,Ar-H), 7.42(2H,d,J=8.8 Hz,Ar-H), 7.20(2H,d,J=8.1 Hz,Ar-H), 7.10 (2H,d,J=8.1 Hz,Ar-H), 6.05(1H,d,J=2.9 Hz,3–CH), 2.35 (6H,s,2–CH₃,Ar–CH₃).
MASS (EI method): 326(M⁺)
Elemental analysis for C₁₈H₁₈N₂O₂S
Calcd.(%) C; 66.23 H; 5.56 N; 8.58
Found(%) C; 66.02 H; 5.51 N; 8.88

Preparation Example 42

4-(4-dimethylaminophenyl)-2-methyl-5-(4-aminosulfonylphenyl)-1H-pyrrole
1H-NMR(DMSO) δ: 7.62(2H,d,J=8.1 Hz,Ar-H), 7.41(2H, d,J=8.1 Hz,Ar-H), 7.12(1H,br-s,NH), 7.05(2H,d,J=8.8 Hz,Ar-H), 6.64(2H,d,J=8.8 Hz,Ar-H), 5.83(1H,d,J=2.9 Hz,3–CH), 2.87(6H,s,NCH₃×2), 2.23(3H,s,2–CH₃).
MASS (EI method): 355(M⁺)
Elemental analysis for C₁₉H₂₁N₃O₂S
Calcd.(%) C; 64.20 H; 5.95 N; 11.82
Found(%) C; 64.03 H; 6.15 N; 12.08

Preparation Example 43

4-(3-dimethylaminophenyl)-2-methyl-5-(4-aminosulfonylphenyl)-1H-pyrrole
1H-NMR(DMSO) δ: 10.85(1H,br-s,NH), 7.65(2H,d,J=8.8 Hz,Ar-H), 7.44(2H,d,J=8.8 Hz,Ar-H), 7.15(2H,br-s, SO₂NH₃), 7.07(1H,t,J=7.8 Hz,Ar-H), 6.56(3H,m,Ar-H), 5.94(1H,d,J=2.0 Hz,3–CH), 2.81(6H,s,NCH₃×2), 2.26(3H, s,2–CH₃).
MASS (EI method): 355(M⁺)
Elemental analysis for C₁₉H₂₁N₃O₂S
Calcd.(%) C; 64.20 H; 5.95 N; 11.82
Found(%) C; 64.28 H; 5.78 N; 11.94

Preparation Example 44

4-(3-chloro-4-N,N-dimethylaminophenyl)-2-methyl-5-(4-aminosulfonylphenyl)-1H-pyrrole
1H-NMR(DMSO) δ: 11.0(1H,br-s,NH), 7.69(2H,d,J=8.3 Hz,Ar-H), 7.43(2H,d,J=8.3 Hz,Ar-H), 7.21(1H,br-s,Ar-H), 7.19(2H,br-s,SO₂NH₂), 7.07(2H,m,Ar-H), 5.94(1H,br-s, 3–CH), 2.73(6H,s,NCH₃×2), 2.25(3H,s,2–CH₃).
MASS (EI method): 389, 391(M⁺)
Elemental analysis for C₁₉H₂₀ClN₃O₂S
Calcd.(%) C; 58.53 H; 5.17 N; 10.78
Found(%) C; 58.58 H; 5.23 N; 10.51

Preparation Example 45

4-(5-N-methylindolyl)-2-methyl-5-(4-aminosulfonylphenyl)-1H-pyrrole
1H-NMR(CDCl₃+CD₃OD) δ: 7.69(2H,d,J=8.1 Hz,Ar-H), 7.59(1H,s,indole), 7.40(2H,d,J=8.1 Hz,Ar-H), 7.26(1H,d,J= 8.8 Hz,Ar-H), 7.15(1H,dd,J=8.8 Hz,1.5 Hz,Ar-H), 7.05(1H, d,J=1.5 Hz,Ar-H), 3.80(3H,s,indole–CH₃), 2.38(3H,s, 2–CH₃).
MASS (EI method): 365(M⁺)
Elemental analysis for C₂₀H₁₉N₃O₂S
Calcd.(%) C; 65.73 H; 5.24 N; 11.50
Found(%) C; 65.49 H; 5.28 N; 11.76

Preparation Example 46

4-ethynyl-2-methyl-5-(4-methylsulfonylphenyl)-1H-pyrrole
1H-NMR(CDCl₃) δ: 8.19(1H,br-s,NH), 7.95(2H,d,J=9.2 Hz,Ar-H), 7.93(2H,d,J=8.8 Hz,Ar-H), 6.16(1H,d,J=2.4 Hz,3–CH), 3.20(1H,s,CC–CH), 3.07(3H,s,SO₂CH₃), 2.32 (3H,s,2–CH₃).
MASS (EI method): 259(M⁺)
Elemental analysis for C₁₄H₁₃NO₂S
Calcd.(%) C; 64.84 H; 5.05 N; 5.40
Found(%) C; 65.12 H; 5.32 N; 5.21

Preparation Example 47

4-propynyl-2-methyl-5-(4-methylsulfonylphenyl)-1H-pyrrole
1H-NMR(CDCl₃) δ: 8.62(1H,br-s,NH), 7.86(2H,d,J=8.8 Hz,Ar-H), 7.75(2H,d,J=8.8 Hz,Ar-H), 6.39(1H,m,3–CH), 3.07(3H,s,SO₂CH₃), 2.42(3H,s,CC–CH₃), 2.34(3H,s, 2–CH₃).
MASS (EI method): 273(M⁺)
Elemental analysis for C₁₅H₁₅NO₂S
Calcd.(%) C; 65.91 H; 5.53 N; 5.12
Found(%) C; 65.79 H; 5.51 N; 4.83

Preparation Example 48

4-phenylethynyl-2-methyl-5-(4-methylsulfonylphenyl)-1H-pyrrole
1H-NMR(CDCl₃) δ: 8.21(1H,br-s,NH), 8.02(2H,d,J=8.4 Hz,Ar-H), 7.95(2H,d,J=8.8 Hz,Ar-H), 7.50(2H,m,Ar-H), 7.35(3H,m,Ar-H), 6.20(1H,d,J=2.0 Hz, 3–CH), 3.08(3H,s, SO₂CH₃), 2.35(3H,s,2–CH₃).
MASS (EI method): 335(M⁺)
Elemental analysis. for C₂₀H₁₇NO₂S
Calcd.(%) C; 71.62 H; 5.11 N; 4.18
Found(%) C; 71.82 H; 5.23 N; 3.98

Preparation Example 49

4-(4-methylphenylethynyl)-2-methyl-5-(4-methylsulfonylphenyl)-1H-pyrrole
1H-NMR(CDCl₃) δ: 8.25(1H,br-s,NH), 8.02(2H,d,J=8.0 Hz,Ar-H), 7.93(2H,d,J=8.8 Hz,Ar-H), 7.39(2H,d,J=8.0 Hz,Ar-H), 7.16(2H,d,J=8.0 Hz,Ar-H), 6.18(1H,m,3–CH), 3.08(3H,s,SO₂CH₃), 2.37(3H,s,Ar–CH₃), 2.34(3H,s, 2–CH₃).
MASS (EI method): 349(M⁺)
Elemental analysis for C₂₁H₁₉NO₂S
Calcd.(%) C; 72.18 H; 5.48 N; 4.01
Found(%) C; 71.83 H; 5.55 N; 3.87

Preparation Example 50

4-(4-fluorophenyl)-5-(4-methylsulfonylphenyl)-1H-pyrrole-2-propionic acid
1H-NMR(CDCl₃) δ: 8.89(1H,br-s,NH), 7.79(2H,d,J=8.8 Hz,Ar-H), 7.41(2H,d,J=8.8 Hz,Ar-H), 7.25(2H,m,Ar-H), 7.00(2H,t,J=8.4 Hz,Ar-H), 6.08(1H,s,3–CH), 3.06(3H,s, SO₂CH₃), 2.98(2H,t,J=6.8 Hz,—CH₂CH₂—), 2.80(2H,t,J= 6.8 Hz,—CH₂CH₂—).
MASS (EI method): 387(M⁺)
Elemental analysis for C₂₀H₁₈FNO₄S
Calcd.(%) C; 62.00 H; 4.68 N; 3.62
Found(%) C; 61.03 H; 4.92 N; 3.87

Preparation Example 51

4-(4-fluorophenyl)-5-(4-methylsulfonylphenyl)-1H-pyrrole-2-n-butyric acid $^1$H-NMR(CDCl$_3$) δ: 9.27(1H,br-s,NH), 7.78(2H,d,J=8.8 Hz,Ar-H), 7.45(2H,d,J=8.8 Hz,Ar-H), 7.26(2H,m,Ar-H), 7.00(2H,t,J=8.8 Hz,Ar-H), 6.07(1H,s,3–CH), 3.07(3H,s,SO$_2$CH$_3$), 2.72(2H,t,J=7.6 Hz,—CH$_2$CH$_2$CH$_2$—) 2.45(2H, t,J=6.8 Hz,—CH$_2$CH$_2$CH$_2$—), 2.00(2H,m,—CH$_2$CH$_2$CH$_2$—).

MASS (EI method): 401(M$^+$)

Elemental analysis for C$_{21}$H$_{20}$FNO$_4$S

Calcd.(%) C; 62.83 H; 5.02 N; 3.49

Found(%) C; 63.09 H; 4.82 N; 3.67

Preparation Example 52

4-(2,3,4-trifluorophenyl)-2-methyl-5-(4-methylsulfonylphenyl)-1H-pyrrole $^1$H-NMR(CDCl$_3$) δ: 8.26(1H,br-s,NH), 7.81(2H,d,J=8.1 Hz,Ar-H), 7.37(2H,d,J=8.8 Hz,Ar-H), 6.93(2H,m,Ar-H), 6.09(1H,s,3–CH), 3.07(3H,s,SO$_2$CH$_3$), 2.39(3H,s,2–CH$_3$).

MASS (EI method): 365(M$^+$)

Elemental analysis for C$^{18}$H$_{14}$F$_3$NO$_2$S

Calcd.(%) C; 59.17 H; 3.86 N; 3.83

Found(%) C; 58.80 H; 3.56 N; 3.66

Preparation Example 53

4-(3-fluoro-5-methylphenyl)-2-methyl-5-(4-methylsulfonylphenyl)-1H-pyrrole $^1$H-NMR(CDCl$_3$) δ: 8.20(1H,br-s,NH), 7.79(2H,d,J=8.8 Hz,Ar-H), 7.43(2H,d,J=8.8 Hz,Ar-H), 6.92(1H,s,Ar-H), 6.77(2H,dd,J=9.6 and 10.8 Hz,Ar-H), 6.08(1H,br-s,3–CH), 3.07(3H,s,SO$_2$CH$_3$), 2.37(3H,s,2–CH$_3$), 2.31(3H,s,Ar–CH$_3$).

MASS (EI method): 343(M$^+$)

Elemental analysis. for C$_{19}$H$_{18}$FNO$_2$S

Calcd.(%) C; 66.45 H; 5.28 N; 4.08

Found(%) C; 66.10 H; 4.98 N; 3.95

Example 1

Tablets; in which the following ingredients are contained.

| | |
|---|---|
| The compound (I) of the invention | 50 mg |
| Lactose | 68 mg |
| Crystalline cellulose | 50 mg |
| Corn starch | 10 mg |
| Carboxymethyl cellulose calcium | 10 mg |
| Magnesium stearate | 2 mg |
| Total | 190 mg |

Example 2

Capsules; in which the following ingredients are contained.

| | |
|---|---|
| The compound (I) of the invention | 50 mg |
| Lactose | 36 mg |
| Crystalline cellulose | 40 mg |
| Corn starch | 50 mg |
| Magnesium stearate | 4 mg |
| Total | 180 mg |

Example 3

Granules; in which the following ingredients are contained.

| | |
|---|---|
| The compound (I) of the invention | 50 mg |
| Lactose | 200 mg |
| Crystalline cellulose | 100 mg |
| Corn starch | 100 mg |
| Carboxymethyl cellulose calcium | 35 mg |
| Hydroxypropyl cellulose | 15 mg |
| Total | 500 mg |

Test Example 1

(Carrageenan Footedema Suppression Test)

The carrageenin footedema suppression test was conducted according to the method of Winter et al. (J. Pharm. Exp. Ther., Vol.141, 369 (1963)). The test samples suspended in Tween 80 were administered orally to SD rats (6 rats per 1 group) in an amount of 1 ml per 100 g of the body weight, while only the solvent was administered in the same manner as above as a control. One hour after the administration, 1% carrageenan physiological saline was injected subcutaneously to the rats in the plantar area of the right hind paw. Three hours after the carrageenan administration, the paw volumes were measured and the edematization rate (%) was calculated with Formula 1 and then edematization suppression rate (%) was calculated with Formula 2.

As a result, the compounds (I) of the invention demonstrated more effective carrageenan footedema suppression action and superior anti-inflammatory action compared to the control compounds (a) and (b).

Edematization rate (%)=((paw volume after carrageenan injection– paw volume before carrageenan injection)/(paw volume before carrageenan injection)×100  Formula: 1

Edematization suppression rate (%)=((edematization rate of control– edematization rate of test samples)/edematization rate of control)×100  Formula: 2

The results of the Test Example 1 are illustrated in Table 1.

TABLE 1

| | Test samples |
|---|---|
| Edematization | Suppression rate (%) |
| Preparation Example 1 | 35.5 |
| Preparation Example 4 | 30.1 |
| Preparation Example 7 | 34.5 |
| Preparation Example 8 | 26.7 |
| Preparation Example 10 | 25.7 |
| Preparation Example 18 | 48.9 |
| Preparation Example 19 | 43.2 |
| Preparation Example 21 | 31.6 |
| Preparation Example 37 | 26.5 |
| Preparation Example 48 | 40.1 |
| Preparation Example 50 | 28.9 |
| Control compound (a) | 23.4 |
| Control compound (b) | −1.8 |

Control compound (a); 4,5-bis(4-methoxyphenyl)-2-methyl-1H-pyrrole (prepared in accordance with the description of Japanese Examined Patent Publication No. 48-38704 (1973))

Control compound (b): 4-(4-fluorophenyl)-5-(4-methylsulfonylphenyl)-1H-pyrrole (prepared in accordance with the description of J. Med. Chem. 37, 988–998 (1994))

Test Example 2

[Rat Adjuvant Arthritis Test]

SD rats were injected subcutaneously with 0.5 mg/kg liquid paraffin/rat of H-37RA strain in the plantar area of the right hind paw. Only liquid paraffin (0.05 ml) was administered to control groups in the same manner. 21 days after the administration, rats showing the evidence of arthritis were selected and divided into groups having equal mean left and right hind paw volumes, and also having equal arthritis scores. From the date of the grouping, the test samples were administered orally to the rats once daily for 7 days (only the solvent was administered to the negative and positive control groups). The degree of the arthritis was quantitatively evaluated by measuring the volumes of the left and right hind paws by using a volume meter (manufactured by Muromachi Kikai) and by scoring the degree of arthritis by macroscopic observation as illustrated in Table 2. According to the scoring criteria in Table 2, 15 is a perfect score.

TABLE 2

| Area | Score | State |
| --- | --- | --- |
| hind paws (left and right) | 0 | normal |
| | 1 | apparent swelling in tarsal area |
| | 2 | swelling in tarsal and talus (ankle) areas, flexion difficulty in joints |
| | 3 | heavy ankylosis (stiffenings in joints, bones, etc.) |
| fore paws (left and right) | 0 | normal |
| | 1 | slight swelling with redness in any area of fingers, nucha area or wrist |
| | 2 | apparent swelling mainly in wrist |
| | 3 | extensive swelling |
| tail | 0 | normal |
| | 1 | joint protrusion perceptible at touch, normal flexion |
| | 2 | protrusion in ⅓ to ½ of the joints, slight flexion difficulty |
| | 3 | protrusion in not less than ½ of joints, stiffening caused tail to become similar to stick |

The right and left hind paw volumes during the period from the starting date of administration of the test samples (day 21) to day 27 are shown in Tables 3 and 4, and arthritis scores measured during the period from the starting date of administration of the test samples (day 21) to day 27 are shown in Tables 5. The dosage of each of the test samples was 3 mg/kg.

As a result, a remarkable decrease in the volumes of the left and right hind paws and a decrease in the arthritis score were noted, and the compound (I) of the invention demonstrated an anti-inflammatory effect substantially equal to the control compound (indomethacin).

TABLE 3

| | Right Hind Paw Volume (ml) | |
| --- | --- | --- |
| Test sample | day 21 | day 27 |
| Preparation Ex. 1 | 3.86 | 2.96 |
| Indomethacin | 3.88 | 2.69 |

TABLE 4

| | Left Hind Paw Volume (ml) | |
| --- | --- | --- |
| Test sample | day 21 | day 27 |
| Preparation Ex. 1 | 2.88 | 2.25 |
| Indomethacin | 2.89 | 2.13 |

TABLE 5

| | Arthritis Score | |
| --- | --- | --- |
| Test sample | day 21 | day 27 |
| Preparation Ex. 1 | 13.2 | 2.25 |
| Indomethacin | 13.8 | 11.4 |

Test Example 3

[Human COX-1 and Human COX-2 Inhibitory Activity Test]

COX-1 and COX-2 activities were measured according to the method of Patrignani et al. (J. Pharm. Exp. Ther. Vol. 271, 1705 (1994)).

(1) COX-1 activity was measured in the following procedure. Blood collected from a healthy normal who had not been taken any nonsteroidal anti-inflammatory drugs (NSAIDs) for at least two weeks was pipetted into glass test tubes by 1 ml and then incubated at 37° C. for 1 hour. The serum obtained by 10 minutes of centrifugation at 2000 rpm at 4° C. was stored at -40° C. until the measurement of the amount of thromboxane $B_2$ ($TXB_2$). The test samples, which had been dissolved in ethanol and diluted to the specified concentrations, were previously dispensed into the glass test tubes, and the solvent was evaporated to dryness by Centrifugal Vaporizer (CVE-200D, manufactured by Tokyo Rika Mfg. Co., Ltd.) so that the test samples were added to the plasma.

(2) COX-2 activity was measured in the following procedure. To blood collected from a healthy normal who had taken 330 mg of aspirin 48 hours before the blood collection in order to inhibit the COX-1 activity, 10 unit/ml of sodium heparin was added, and then pipetted into glass test tubes by 1 ml. 10 μg/ml of Lipopolysaccharide (LPS) was added thereto and the plasma obtained by the specified operation was stored at −40° C. until the measurement for the amount of prostaglandin $E_2$ ($PGE_2$). Test samples containing the test samples were treated in the same manner of operation as described above.

(3) The measurement for the $TXB_2$ content was conducted in the following procedure. In a part of a 96 well plate coated with anti-rabbit IgG antibody, 2 wells were allotted respectively to blank well, Non-specific Binding (NSB) well, Maximum Binding ($B_0$) well, standard wells at 7 concentrations of TXB$_2$ (1000 pg/ml) in doubling dilution ranging from 1000–15.6 pg/ml. The rest of the wells were used for the measurement of the samples. EIA buffer was added to the NSB wells (100 μl) and B$_0$ wells (50 μl), respectively. 50 μl of each of the standard dilution was added in an order from thinner to thicker concentrations. Each of the samples was added to the rest of the wells in an amount of 50 μl. Then, 50 μl of TXB$_2$ tracer was added to each of the wells except for the blank wells. Further, 50 μl of TXB$_2$ antibody was added to each of the wells except for the NSB wells and blank wells, then the well plate was covered with a plastic film and the reaction continued for 18 hours at room temperature. When the reaction was terminated, the wells were washed 5 times with a wash buffer. 200 μl of Elman's reagent was added to each of the wells and then the well plate was covered with a plastic film and developed for 60 minutes in a dark place. The absorbance at 405 nm was measured by an Immuno Reader (NJ-2000, manufactured by Nippon Intermed Co., Ltd.). From the measurement result, %B/B$_0$ was calculated and, applying it to the approximation formula of Hill Plot, the concentration of the samples was determined to be 2,000 times concentration.

(4) The measurement for the PGE$_2$ content was conducted in the following procedure. In a part of 96 well plate coated with goat anti-mouse antibody, 2 wells were alloted respectively to a blank well, Non-specific Binding (NSB) well, Maximum Binding (B$_0$) well, standard wells at seven concentrations of PGE$_2$ (1000 pg/ml) in doubling dilution ranging from 1000–15.6 pg/ml. The rest of the wells were used for the sample measurement. EIA buffer was added to the NSB wells (100 μl) and to the B$_0$ wells (50 μl), respectively. 50 μl of each of the standard dilution was added in an order from thinner to thicker concentrations. Each of the samples was added to the rest of the wells in an amount of 50 μl. Then, 50 μl of PGE$_2$ tracer was added to each of the wells except for blank wells. Further, 50 μl PGE$_2$ monoclonal antibody was added to each of the wells except for the NSB wells and blank wells, then the well plate was covered with a plastic film and the reaction continued at room temperature for 18 hours. When the reaction was terminated, the wells were washed 5 times with a wash buffer. 200 μl of Elman's reagent was added to each of the wells, and then the well plate was covered with a plastic film and developed for 60 minutes in a dark place. The absorbance at 405 nm was measured by an Immuno Reader (NJ-2000, manufactured by Nippon Intermed Co., Ltd.). From the measurement result, %B/B$_0$ was calculated and, applying it to the approximation formula of Hill Plot, the concentration of the samples was determined to be 40 times concentration. The dilution was conducted with an EIA buffer throughout the Test Example 3. The COX-1 inhibitory activity was measured at concentrations ranging from $10^{-5}$M to $10^{-6}$M (regarding the preparation Example 1 and comparative compound (c), the range was from $10^{-4}$M to $10^{-6}$M) and the COX-2 inhibitory activity was measured at concentrations ranging from $10^{-5}$M to $10^{-7}$M, and IC$_{50}$ was obtained calculatively by applying the measured values to the approximation formula of Hill Plot.

As a result, the compounds (I) of the invention demonstrated strong inhibitory activity selective to COX-2.

The results of the Test Example 3 are illustrated in Table 6.

TABLE 6

Inhibitory Activity (IC$_{50}$; μM)

| Test sample | COX-1 | COX-2 | COX-1/COX-2 |
|---|---|---|---|
| Prep. Ex. 1 | 649.0 | 0.95 | 683 |
| Prep. Ex. 4 | 100< | 0.164 | 610< |
| Prep. Ex. 7 | 30.6 | 0.144 | 212 |
| Prep. Ex. 8 | 26.7 | 0.219 | 457< |
| Prep. Ex. 10 | 84.0 | 0.274 | 307 |
| Prep. Ex. 11 | 9.9 | 0.084 | 118 |
| Prep. Ex. 18 | 12.6 | 0.123 | 102 |
| Prep. Ex. 19 | 100< | 0.747 | 134< |
| Prep. Ex. 21 | 39.2 | 0.129 | 304 |
| Prep. Ex. 23 | 100< | 0.346 | 289< |
| Prep. Ex. 28 | 100< | 0.31 | 323< |
| Prep. Ex. 32 | 100< | 0.442 | 226< |
| Prep. Ex. 37 | 100< | 0.14 | 714< |
| Prep. Ex. 48 | 100< | 0.3 | 339< |
| Prep. Ex. 50 | 100< | 0.454 | 220< |
| Prep. Ex. 52 | 50.4 | 0.11 | 458 |
| Prep. Ex. 53 | 100 | 0.162 | 617 |
| Control Compound (a) | 0.001 | 4.82 | 0.1> |
| Control Compound (b) | 373 | 12.67 | 29.4** |
| Control Compound (c) | 183 | 0.44 | 416 |
| Indomethacin | 0.893 | 0.208 | 4.3 |

**Value specified in the literature.

Control Compound (c); N-(2-cyclohexyloxy-4-nitrophenyl) methanesulfonamido (prepared in accordance with the description of Japanese Enexamined Patent Publication No. 62-292856 (1987)).

Test Example 4

(Antipyretic Action Test With Respect To Brewer's Yeast Fever)

The antipyretic action was measured as described in the following. A sensor was inserted into the rectum of each rats and the body temperature of one hour after the insertion was recorded as the basal body temperature. The rats were injected subcutaneously with 2 ml/body of 20% brewer's yeast at the region of back and, 18 hours after the injection, the intrafebrile body temperatures were measured. Rats who had shown not less than 0.75° C. of body temperature elevation were selected to whom the test samples was administered orally. The body temperatures of the selected rats were measured every one hour for the following 5 hours. The dosage of each of the test samples was 10 mg/kg.

As a result, the antipyretic action of the compound (I) of the invention continued for 5 hours after administration and demonstrated the antipyretic action substantially equal to that of the control compound (c). The result of the Test Example 4 is illustrated in Table 7.

TABLE 7

| Test Compound | Basal Body Temperature (° C.) | Intrafebrile Body Temperature (° C.) | 1 Hour After (° C.) | 3 Hours After (° C.) | 5 Hours After (° C.) |
|---|---|---|---|---|---|
| Prep. Ex. 1 | 37.54 | 39.08 | 37.98 | 37.10 | 37.13 |
| Control Compound (c) | 37.41 | 38.89 | 37.67 | 37.04 | 37.12 |

Test Example 5

(Analgesic Action Test)

The analgesic action test was conducted according to the method of Randall et al. [Arch 1970 int. pharmacodyn. Ther. Vol. 111, 409 (1957)].

SD rats (6 rats per group) fasted overnight were employed for the test. After the measurement of pain threshold values of the left and right hind paws twice using an analgesimeter, the rats were injected subcutaneously with 0.1 ml of 20% brewer's yeast solution at the plantar area of the right hind paw to elicit inflammation. Two hours after the elicitation of inflammation, the pain threshold values of the left and right hind paws were measured and, immediately after the measurement, the test samples were administered orally to the rats. Three hours after the administration, the pain threshold values of the left and right hind paws were measured. The pain threshold value rising rate (%) was calculated with respect to the right hind paw with the Formula 3, and the pain threshold value fluctuation rate (%) was calculated with respect to the left hind paw with the Formula 4. The dosage amount of each of the test samples was 3 mg/kg.

Pain threshold value rising rate (%)=((pain threshold value of 3 hours after drug administration–pain threshold value of 2 hours after yeast administration)/(pain threshold value before yeast administration–pain threshold value of 2 hours after yeast administration))×100   Formula: 3

Pain threshold value fluctuation rate (%)=(1 –(pain threshold value of 3 hours after drug administration/pain threshold value of 2 hours after yeast administration))×100   Formula: 4

As a result, the compounds (I) of the invention demonstrated greater pain threshold value rising rate with respect to the inflammatory paw compared to the comparative compound (c) and exerted no influence on the threshold value fluctuation with respect to the non-inflammatory paw in the same manner as control compound (c), thereby to prove an excellent analgesic action. The result of the Test Example 5 is illustrated in Table 8.

TABLE 8

| Test Article | Pain Threshold Value Rising Rate (%) Right Hind Paw (inflammatory paw) | Pain Threshold Value Fluctuation Rate (%) Left Hind Paw (non-inflammatory paw) |
| --- | --- | --- |
| Prep. Ex. 1 | 33.3 | 2.47 |
| Comp. Ex. (c) | 24.0 | −1.46 |

Test Example 6

[Gastric Injury Test]

SD rats fasted overnight and received no water from 2 hours before the administration of the test samples were employed for the present test. 6 hours after the administration of the test samples, the rats were sacrificed to extirpate stomachs into which 8 ml of 20% formalin was injected. Each of the stomachs was incised along the greater curvature after gastropexy, and the length of the gastric injury was measured by a stereoscopic microscope. The dosage amounts were 30 mg/kg and 1000 mg/kg regarding the compounds (I) of the invention, and 30 mg/kg regarding indomethacin.

As a result, no gastric ulcer often caused by nonsteroidal anti-inflammatory drugs was noted in the present test, thereby the compounds (I) of the invention indicated the possibility for an anti-inflammatory drug with minimum adverse side effects.

The result of the Test Example 6 is illustrated in Table 9.

TABLE 9

| | Length of the Gastric Injury (mm) | |
| --- | --- | --- |
| Test sample | 30 mg/kg | 1000 mg/kg |
| Prep. Ex. 1 | 0 | 0 |
| Indomethacin | 41.5 | — |

Test Example 7

[Cytostatic Action Test on Various Cells]

The cytostatic measurement of the various cancer cells were conducted according to the method of the U.S. National Cancer Institute (NCI). Adhesive cells such as CaCo-2 and HepG2 were adjusted in each of the specified culture mediums at $0.5 \times 10^5$ cells/ml concentration and pipetted into a 96 well-plate (Costar3695) in an amount of 100 μl/well. The cells were cultured under the conditions of at 37° C. in 5% $CO_2$ atmosphere for 24 hours to allow the cell adhesion, and then the numbers of each of the cells were determined by the XTT method to be recorded as the cell number of day 0 ($C_{0days}$). After that, only the medium solutions were exchanged in the control groups, and culture mediums each containing the test samples adjusted to each of the specified concentrations were exchanged In the test sample dispensing groups, then the cells were cultured under the conditions of at 37° C. in 5% $CO_2$ atmosphere for 72 hours. The numbers of each of the cells were determined by the XTT method to be recorded as the cell number of day 3 ($C_{3days}$). Further, only the medium solutions were pipetted into the control groups and the test sample administration groups were adjusted to $5 \times 10^5$ cells/ml concentrations in each of the specified culture mediums containing the test samples adjusted to each of the specified concentrations, then pipetted into a 96 well-plate (Costar3695) in an amount of 100 μl/well. The cells were cultured under the condition of at 37° C. in 5% $CO_2$ atmosphere for 72 hours, and the number of each of the cells ($T_{3days}$) were determined in the same manner. From the result, the cell proliferation rate with respect to the control groups was calculated with the Formula 5, and $IC_{50}$ with respect to the cell proliferation rate was obtained from the cell proliferation rate-concentration curve.

As a result, the compounds of Preparation Examples 1 and 37 demonstrated a cytostatic action with respect to CaCo-2 cells which are the colon cancer cells.

Cell proliferation rate (%) with respect to control groups=
[($T_{3days}-C_{0days}$)/($C_{3days}-C_{0days}$)]×100   Formula: 5

The result of the Test Example 10 is illustrated in Table 10.

TABLE 10

| | Cytostatic rate ($IC_{50}$: μM) |
| --- | --- |
| Test Samples | CaCo-2 (cancer cell tumor) |
| Preparation Example 1 | 0.78 |
| Preparation Example 37 | 0.95 |
| Mitomycin C | >1 |
| 5-fluorouracil | 3.30 |

Test Example 8

(Apoptosis Induction Test in CaCo-2 Cells)

CaCo-2 cells were adjusted in 10% FBS/DMEM/NEAA to $1.0 \times 10^5$ cells/ml concentration and then pipetted into a 6 well plate in an amount of 3 ml/well. The cells were cultured under the conditions of at 37° C. in 5% $CO_2$ atmosphere for 24 hours to allow the cell adhesion. Only the medium solution (0.1% ethanol) was exchanged in the control group, and the compound of the invention (Preparation Example 1) group was transferred to culture mediums containing the compound adjusted to each of the specified concentrations, then the cells were cultured under the condition of at 37° C. in 5% $CO_2$ atmosphere for 24 hours. Then the culture medium and the adhesive cells separated of the adhesion by trypsin were collected and centrifuged at 1000 rpm for 5 minutes to remove the supernatant. The cells were washed with PBS(–) and then 20 μl of 90% ethanol/0.5% triton× 100/10mM EDTA/10mM Tris-HCl (pH7.4) and 5 μl of propidium iodide (1 μg/ml) were added thereto to stain the nucleuses. A drop of the stained cell solution was placed on a preparation glass to be examined by a fluorescence microscope at B range. As a result, cell apoptosis caused by the compound of the invention was observed.

Test Example 9

[Antitumor Effect with respect to Sarcoma 180 Solid Tumor Mouse]

The antitumor effect test was conducted according to the method of the U. S. National Cancer Institute (NCI) (*Cancer Chemotherapy Reports part* 3, Vol. 3, 1 (1978)). Cell suspension of Sarcoma 180 cells (mouse sarcoma virus) which was employed as the tumor cell strain for transplant was prepared by diluting the cells in the Hank's solution at $2 \times 10^7$ cells/ml concentration ($5 \times 10^6$ cells/mouse), and ICR mice (10 mice per group) aged 5 weeks were injected subcutaneously with 0.2 ml of the cell suspension at the region of the back. Setting the day of the tumor transplantation as day 0. the mice were administered in the abdominal cavity with the compounds of the invention (Preparation Examples 1 and 37), 5-fluorouracyl, and the solution as the control for 10 days consecutively from day 1. On day 11, the mice were sacrificed, and portions of the solid tumor were removed so that weights thereof were measured. The result of the Test Example 9 is illustrated in Table 11. The dosage of each of the test samples was 10 mg/kg.

As a result, an advantageous decrease in the tumor weight compared to the control groups was noted, thereby indicated that the compounds of the invention have an excellent antitumor action.

TABLE 11

| Test sample | Tumor Weight (g) |
| --- | --- |
| Control | 2.125 |
| Preparation Example 1 | 0.726 |
| Preparation Example 37 | 0.906 |
| 5-fluorouracyl | 0.930 |

Test Example 10

[Acute Toxicity Test]

SD rats (3 rats per group) fasted overnight was employed in the present test. The title compound (Preparation Example 1) suspended in 1% methyl cellulose was administered to the rats. The test was conducted on the dosages of 500/kg, 1000/kg, and 2000/kg. The general symptoms and life or death of the rats were observed for a week after the administration. In all the groups, an analgesic action was noted after the administration, and the rats recovered to the normal state in one hour. Further, no death was noted in the test. In the inspection after one week from the administration, the weight increased favorably and no abnormality was noted in the general symptoms. It was indicted from the test result that the title compounds ensure the enhanced safety.

Test Example 11

[Subcute Toxicity Test]

The Subcute toxicity test was conducted as described in the following. SD rats (six each of male and female rats per group) were employed in the present test. The title compound (Preparation Example 1) was suspended in 0.5% methyl cellulose solution to be administered to the rats by a disposable feeding tube (manufactured by Fuchigami Kikai) once daily for 14 days. The dosage of the test samples was 100 mg/kg. During the administration period, neither of a change in the general symptoms nor an adverse affect on the weight increase was noted. Thus, the title compound exhibited the enhanced safety.

What is claimed is:
1. A compound of the general formula (I):

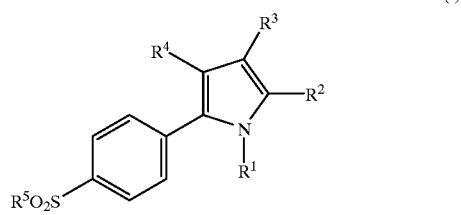

wherein
R$^1$ represents a hydrogen atom or lower alkyl group;
R$^2$ represents a lower alkyl group or $(CH_2)_{n1}COOH$ and n1 is 1, 2 or 3;
R$^3$ represents a hydrogen atom, halogen atom, lower alkyl group, hydroxymethyl group, carboxyl group, lower alkoxycarbonyl group, lower alkoxymethyl group, carbamoyl group, mono-lower alkylcarbamoyl group or di-lower alkylcalbamoyl group;
R$^4$ represents a phenyl group, dicyclic heteroaryl group or phenyl ethynyl group which may optionally be substituted by a functional group selected from the group consisting of a lower alkyl group, halogen atom, lower alkoxy group, lower alkylthio group, nitro group, alkanoyl group, cyano group, amino group, mono-lower alkylamino group, di-lower alkylamino group, alkanoylamino group or alkanoyloxy group; or lower alkynyl group;
R$^5$ represents a lower alkyl group, amino group, mono-lower alkylamino group or di-lower alkylamino group, and a salt thereof.
2. A compound of claim 1 wherein R$^1$ is a hydrogen atom or methyl group, and a salt thereof.
3. A compound of claim 1 wherein R$^2$ is a methyl group, ethyl group or $(CH_2)_2COOH$, and a salt thereof.
4. A compound of claim 1 wherein R$^3$ is a hydrogen atom, and a salt thereof.
5. A compound of claim 1 wherein R$^4$ is a phenyl group which is substituted by one to three functional groups selected from the group consisting of a lower alkyl group, halogen atom, lower alkoxy group, lower alkylthio group, nitro group, alkanoyl group, cyano group, amino group, mono-lower alkylamino group, di-lower alkylamino group, alkanoylamino group or alkanoyloxy group, 6-N-methylindolyl, 5-N-methylindolyl, 5-(2,3-dihydrobenzofuranyl), 6-(2,3-dihydrobenzofuranyl), 4-(3,4-methylenedioxyphenyl), 3-(3,4-methylenedioxyphenyl) or phenylethynyl group, and a salt thereof.

6. A compound of claim 1 wherein $R^4$ is a phenyl group which is substituted by one to three functional groups selected from the group consisting of a methyl group, fluorine atom, chlorine atom, methoxy group, methylthio group, amino group, methylamino group and dimethylamino group, 6-N-methylindolyl, 5-N-methylindolyl, 5-(2,3-dihydrobenzofuranyl), 6-(2,3-dihydrobenzofuranyl) or phenylethynyl group, and a salt thereof.

7. A compound of claim 1 wherein $R^5$ is a methyl group or amino group and a salt thereof.

8. A compound of claim 1 wherein $R^1$ and $R^3$ are H, $R^2$ is lower alkyl, $R^4$ is a phenyl group substituted by one to three functional groups selected from the group consisting of a methyl group, fluorine atom, chlorine atom, methoxy group, amino group, methylamino group, methylthio group and dimethylamlno group, 6-N-methylindolyl, 5-N-methylindolyl, 5-(2,3-dihydrobenzofuranyl), 6-(2,3-dihydrobenzofuranyl) or phenylethynyl group and $R^5$ is a methyl group, and a salt thereof.

9. A compound of claim 1 represented by the following formula:

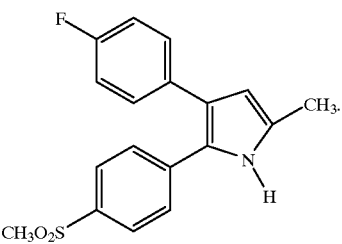

10. An antitumor agent comprising the compound of claim 1 or the salt thereof as an active ingredient.

11. An anti-inflammatory agent comprising the compound of claim 1 or the salt thereof as an active ingredient.

12. A method of treating tumors which comprises administering to a subject an effective amount of the compound of claim 1 or the salt thereof.

13. A method of treating inflammation which comprises administering to a subject an effective amount of the compound of claim 1 or the salt thereof.

14. A COX-2 selective inhibitor which is the compound of claim 1 or the salt thereof.

15. A method of COX-2 selective inhibition which comprises administering to a subject an inhibitory effective amount of the compound of claim 1 or the salt thereof.

16. A pharmaceutical composition comprising the compound of claim 1 or the salt thereof, and a pharmaceutically acceptable carrier.

* * * * *